US008846868B2

(12) United States Patent
Caswell et al.

(10) Patent No.: US 8,846,868 B2
(45) Date of Patent: Sep. 30, 2014

(54) ANTI-AREG/HB-EGF ANTIBODIES AND TREATMENT

(75) Inventors: Jill Caswell, Belfast (GB); Shane Olwill, Belfast (GB); James Johnston, Belfast (GB); Richard Buick, Belfast (GB); Thomas Jaquin, Belfast (GB); Declan Doherty, Belfast (GB); Christopher Scott, Belfast (GB)

(73) Assignee: Fusion Antibodies Limited, Belfast (GB)

(*) Notice: Subject to any disclaimer, the term of this patent is extended or adjusted under 35 U.S.C. 154(b) by 313 days.

(21) Appl. No.: 12/988,135

(22) PCT Filed: Apr. 17, 2009

(86) PCT No.: PCT/GB2009/050389
§ 371 (c)(1),
(2), (4) Date: Mar. 7, 2011

(87) PCT Pub. No.: WO2009/127881
PCT Pub. Date: Oct. 22, 2009

(65) Prior Publication Data
US 2011/0150886 A1    Jun. 23, 2011

(30) Foreign Application Priority Data

Apr. 17, 2008    (GB) ................................. 0807018.7

(51) Int. Cl.
| | | |
|---|---|---|
| *C07K 16/00* | (2006.01) | |
| *C12P 21/08* | (2006.01) | |
| *C07K 16/22* | (2006.01) | |
| *A61K 39/395* | (2006.01) | |
| *C07K 16/28* | (2006.01) | |
| *A61K 39/00* | (2006.01) | |

(52) U.S. Cl.
CPC ........... *C07K 16/22* (2013.01); *A61K 2039/505* (2013.01); *C07K 2317/31* (2013.01); *C07K 2317/74* (2013.01); *C07K 2317/33* (2013.01); *C07K 2317/73* (2013.01); *A61K 39/39558* (2013.01); *C07K 16/2863* (2013.01)
USPC ..................................... 530/387.1; 530/388.1

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 4,816,567 A | 3/1989 | Cabilly et al. | |
| 4,892,538 A | 1/1990 | Aebischer et al. | |
| 5,283,187 A | 2/1994 | Aebischer et al. | |
| 5,567,588 A | 10/1996 | Gold et al. | |
| 5,830,995 A | 11/1998 | Shoyab et al. | |
| 5,849,902 A | 12/1998 | Arrow et al. | |
| 6,699,843 B2 | 3/2004 | Pietras et al. | |
| 6,867,289 B1 | 3/2005 | Gorenstein et al. | |
| 6,994,856 B1 * | 2/2006 | Godowski et al. | .......... 424/178.1 |
| 7,851,601 B2 * | 12/2010 | Mekada et al. | .......... 530/388.24 |
| 2003/0078222 A1 * | 4/2003 | Ghildyal et al. | ................ 514/44 |
| 2007/0003523 A1 * | 1/2007 | Tolentino et al. | ............ 424/93.2 |
| 2009/0318346 A1 * | 12/2009 | Bacus et al. | .................... 514/12 |
| 2011/0110956 A1 * | 5/2011 | Rothe et al. | ................ 424/158.1 |

FOREIGN PATENT DOCUMENTS

| | | |
|---|---|---|
| WO | 93/25673 | 12/1993 |
| WO | 99/07409 | 2/1999 |
| WO | 99/32619 | 7/1999 |
| WO | 00/01846 | 1/2000 |
| WO | 00/44895 | 8/2000 |
| WO | 00/44914 | 8/2000 |
| WO | 01/29058 | 4/2001 |
| WO | 01/36646 | 5/2001 |
| WO | 03/047586 | 6/2003 |
| WO | 2004/068931 | 8/2004 |
| WO | 2004/073734 | 9/2004 |
| WO | 2005/014577 | 2/2005 |
| WO | 2005/053739 | 6/2005 |
| WO | 2005/117877 | 12/2005 |
| WO | 2006/044748 | 4/2006 |
| WO | 2008/044068 | 4/2008 |
| WO | 2009/040134 | 4/2009 |

OTHER PUBLICATIONS

Paul, Fundamental Immunology, 3rd Edition, 1993, pp. 292-295.*
Rudikoff et al., Proc. Natl. Acad. Sci. USA, 79(6):1979-1983, Mar. 1982.*
Colman, Research in Immunology, 145:33-36, 1994.*
Bendig, Methods: A Companion to Methods in Enzymology, 1995; 8:83-93.*
Azzariti et al., "The schedule-dependent enhanced cytotoxic activity of 7-ethyl-10-hydroxy-camptothecin (SN-38) in combination with Gefitinib (Iressa$^{TM}$, ZD1839)," *Biochemical Pharmacology*, vol. 68. pp. 135-144 (2004).
Bayes et al., "Gateways to Clinical Trials," *Methods and Findings in Experimental and Clinical Pharmacology*, vol. 26, No. 7, pp. 587-612 (2004).
Buzzi et al., "CRM1 97 (nontoxic diphtheria toxin): effects on advanced cancer patients," *Cancer Immunology Imununotherapy*, vol. 53, pp. 1041-1048 (2004).
Mahtouk et al., "Amphiregulin Is Produced by Myeloma Cells and Is Involved in Tumor-Environment Interactions in Multiple Myeloma," *Blood*, vol. 104: Abstract 4306 (2004).

(Continued)

*Primary Examiner* — Hong Sang
(74) *Attorney, Agent, or Firm* — Drinker, Biddle & Reath, LLP

(57) ABSTRACT

Described are cross-specific antibody molecules with binding specificity for both AREG and HBEGF. The antibody molecules may be used in methods of treatment of cancer and diseases associated with angiogenesis.

11 Claims, 25 Drawing Sheets

(56) References Cited

OTHER PUBLICATIONS

Mahtouk et al., "Syndecan-1 Is Essential for the Myeloma Cell Growth Factor Activity of EGF-Family Ligands in Multiple Myeloma," *Blood*, vol. 106: Abstract 626 (2005).
Amsellem-Ouazana et al., "Gene Expression Profiling of ERBB Receptors and Ligands in Human Transitional Cell Carcinoma of the Bladder," *The Journal of Urology*, vol. 175, pp. 1127-1132 (2006).
Dennis, "Cancer: Off by a wisker," *Nature* 442:739-741 (2006).
Cespdes et al., "Mouse models in oncogenesis and cancer therapy," *Clin. Transl. Oncol.* 8(5):318-329 (2006).
Talmadge et al., "Murine Models to Evaluate Novel and Conventional Therapeutic Strategies for Cancer," *Am. J. Pathol* 170(3):793-804 (2007).
Thurber et al, "Antibody tumor penetration," *Adv. Drug Deliv. Rev.* 60:1421 (2008).
Beckman et al., "Antibody Constructs in Cancer Therapy," *Can.* 109:170-179 (2006).
Fujimori et al., "A Modeling Analysis of Monoclonal Antibody Percolation Through Tumors: A Binding-Site Barries," *J. Nuc. Med.* 31:1191-1198 (1990).
Rudnick et al., "Affinity and Avidity in Antibody-Based Tumor Targeting," *Can. Biotherp. & Radiopharm.* 24: 155-162 (2009).
Voskoglou-Nomikos et al., "Clinical Predictive Value of the in Vitro Cell Line, Human Xenograft, and Mouse Allograft Preclinical Cancer Models," *Clin. Can. Res.* 9:4227-4239 (2003).
de Bono et al., "The ErbB receptor family: a therapeutic target for cancer," *Trends in Molecular Medicine*, vol. 8, No. 4, pp. S19-S26 (2002).
Motoyama et al., "The Efficacy of ErbB Receptor-targeted Anticancer Therapeutics Is Influenced by the Availability of Epidermal Growth Factor-related Peptides,"*Cancer Research*, vol. 62, No. 11, pp. 3151-3158 (2002).
Smith et al., "The efficacy of Herceptin therapies is influenced by the expression of other erbB receptors, their ligands and the activation of downstream signaling proteins," *British Journal of Cancer*, vol. 91, pp. 1190-1194 (2004).
Miyamoto et al., "Heparin-Binding EGF-Like Growth Factor Is a Promising Target for Ovarian Cancer Therapy," *Cancer Research*, vol. 64, No. 16, pp. 5720-5727 (2004).
Miyamoto et al., "Heparin-binding epidermal growth factor-like growth factor as a novel targeting molecule for cancer therapy," *Cancer Science*, vol. 97, pp. 341-347 (2006).
Menendez et al., "Trastuzurnab in Combination With Heregulin-Activated Her-2 (*erbB-2*) Triggers a Receptor-Enhanced Chemosensitivity Effect in the Absence of Her-2 Overexpression," *Journal of Clinical Oncology*, vol. 24, No. 23, pp. 3735-3746 (2006).

\* cited by examiner

```
AREG       (1)  MRAPLPPAPVVLSLLILGSGHYAAGLDLNDTYSGKREPFSGDHSADGFE          50
HBEGF      (1)  ---MKLLPSVVLKLFLAAVLSALVTGESLERLRRG---LAAGTSNPDPPT
Consensus  (1)             L PA VL  L                  G      AG  D AREG      (51)  VTSRSEMSSGSEISPVSEMPSSSEPSSGADYDYSEEYDNEPQIPGYIVDD         100
HBEGF     (45)  VSTDQLLPLGG-----------------GRDRKVRDLQEAD-------LD
Consensus (51)  VSS     L G                      G D    D D D      D AREG     (101)  SVRVEQVVKPPQNKTESENTSDKPKRKKKG-GKNGNRRNRKKKNPCNAEF         150
HBEGF     (71)  LLRVTLSSKPQALATP---NKEEHGKRKKKGKGLGK----KRDPCLRKY
Consensus(101)  LRV     KP        T N D  KRKKKG  GK             KK PC   F AREG     (151)  QNFCIHGECKYIEHLEAVTCKCQQEYFGERCGEKSMKTHSMIDSSLSKIA         200
HBEGF    (113)  KDFCIHGECKYVKELRAPSCICHPGYHGERCHGLSLPVENRLYTYDHTTI
Consensus(151)  FCIHGECKYI  L  A  SC C       Y GERC         SL    I S AREG     (201)  LAATAAFMSAVILTAVAVITVQLRRQYVRKYEGEAEERKKLRQENGNVHA         250
HBEGF    (163)  LAVVAVVLSSVCLLVIVGLLMFRYHRRG-GYDVENEEKVKLGMTNSH---
Consensus(201)  LA    A    LSAV L I I M           YD E EEK KL N AREG     (251)  IA-
HBEGF    (209)  ---
Consensus(251)
```

Figure 5

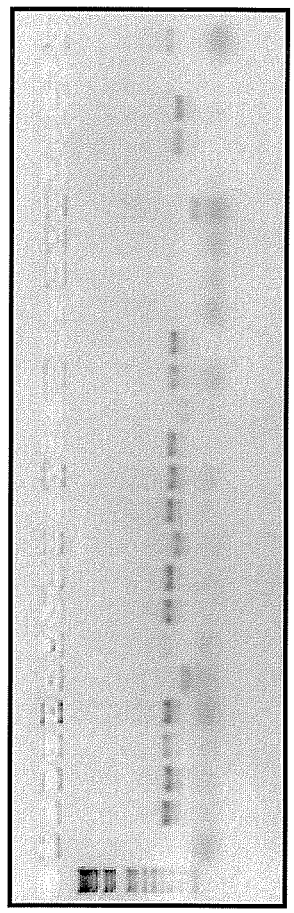
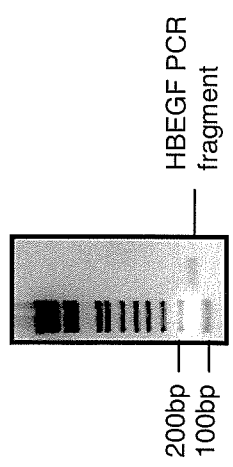
Figure 6a
Figure 6b

\* p< 0.05
\*\* p< 0.001

ANTI-AREG/HB-EGF ANTIBODIES AND TREATMENT

FIELD OF THE INVENTION

The present invention relates to cancer treatment. In particular it relates to methods of determining susceptibility to resistance to anti-cancer drugs, methods for overcoming such resistance and combination therapies for the treatment of cancer.

BACKGROUND TO THE INVENTION

Cancer is the leading cause of mortality in the Western countries. A large number of chemotherapeutic agents have been developed over the last 50 years to treat cancers. The majority of chemotherapeutic agents can be classified into one of the following groups: alkylating agents, antimetabolites, anthracyclines, plant alkaloids, topoisomerase inhibitors, and antitumour agents. All of these drugs affect cell division or DNA synthesis and function in some way.

The effectiveness of particular chemotherapeutic agents varies between cancers, between patients and over time in individual patients. Cancerous cells exposed to a chemotherapeutic agent may develop resistance to such an agent, and quite often cross-resistance to several other antineoplastic agents as well. Moreover, the narrow therapeutic index of many chemotherapeutic agents further limits their use. Accordingly, it is often necessary to change treatments of patients with cancer if the first or second line therapy is not sufficiently effective or ceases to be sufficiently effective. In many cases combinations of particular treatments have been found to be particularly effective.

These chemotherapeutics agents, 5-Fu included, can be used alone but it is common that clinical regimes incorporate a combination. Indeed combined chemotherapy has shown promising results by improving the response rates in patients by acting on the tumors through different pathways. Nevertheless many patients still cannot be treated through these regimes because of drug resistance, either acquired or inherent.

Further, the choice of chemotherapy is further complicated by cancer type and, for example, whether or not the cancer is associated with a p53 mutation. For example, as described in WO2005/053739, whereas the combination of platinum based chemotherapeutics with antiFas antibodies was shown to have a synergistic cytotoxic effect in tumours with wild type p53, such synergy was not seen in p53 mutant cells.

5-Fu, CPT-11 and oxaliplatin remain front line therapies, but the development of non responsive tumours or chemotherapy resistant cancer remains a major obstacle to successful chemotherapy. Due to the importance of early treatment of cancers, there is a clear need for tools which enable prediction of whether a particular therapy, either single or combination, will be effective against particular tumours in individual patients. Moreover, there remains the need for new treatment regimes to increase the repertoire of treatments available to the physician.

As described in the inventors' copending international application PCT/GB2007/050623, the present inventors have investigated proteins upregulated in response to treatment with different classes of chemotherapy and have surprisingly shown that a variety of genes encoding peptide growth factors of the Epidermal Growth Factor (EGF) family are overexpressed in a number of different tumour cell line models of cancer from a number of different types of cancer following in vivo challenge with different physiologically relevant doses of different classes of chemotherapy.

The inventors have also shown that combinations of inhibitors of different EGFs resulted in a surprisingly dramatic reduction in tumour cell growth and proliferation compared to the reduction when inhibitors of a single EGF were tested.

SUMMARY OF THE INVENTION

The inventors have further developed the use of chemotherapeutic strategies employing the targeting of two or more EGFs by the development of multispecific antibodies which specifically bind two or more different EGFs. Moreover, binding of the antibodies to tumour cells was found to be enhanced after chemotherapy treatment. Different EGFs are expected to be upregulated in different cancers. Accordingly, the development of polyspecific antibodies which can bind more than one EGF has significant advantages for use both in the clinic and in the lab. The development of bispecific antibodies can target the different hallmarks of cancer. For example, HBEGF has been shown to be associated with cell motility and proliferation and also angiogenesis. AREG expression increases cell invasiveness. Therefore an antibody that targets both HBEGF and AREG may have significant effect on these characteristics.

Accordingly, in a first aspect of the present invention, there is provided a polyspecific antibody which binds at least two, such as three or four, different EGF molecules. In one embodiment, the antibody specifically binds two, three or four of the EGFs selected from HB-EGF, AREG, EREG, BTC or TGFα.

In one embodiment, the antibody molecule has an affinity for each of two EGFs of at least $10^{-7}$ M, for example at least $10^{-8}$ M, or higher e.g. 10 9 M, or higher.

In one embodiment, the antibody molecule is bispecific.

Such polyspecific antibodies may be generated using any known method in the art. One method of generating bispecific antibodies is to engineer artificial antibodies produced by chemical crosslinking, fusion of hybridoma cells, or by molecular genetic techniques to have one pair of heavy and light chains with binding specificity for a first antigen and a second pair of heavy and light chains with binding specificity for a second antigen. In such embodiments, the epitopes of the two targets are generally unrelated. However, the present inventors have employed a strategy of selecting a conserved region in the peptide sequence of two EGFs, for example HBEGF and AREG, and raised monoclonal antibodies to said region. By employing this technique, antibodies with multiple specificities can be made without the need for engineering. This approach leads to the development of a functional antibody in a cost effective and timely manner.

Accordingly, in one embodiment of the present invention, the polyspecific antibody is a monoclonal antibody raised against a single antigen. In one embodiment, the single antigen comprises, preferably consists of, a polypeptide having an amino acid sequence having at least 70%, such as at least 80%, at least 90% or at least 95% sequence identity with corresponding sequences in each of the EGFs to which it binds.

In one embodiment of the invention, the polyspecific antibody is a bispecific antibody having binding specificity for HBEGF and AREG. In one embodiment, the antibody molecule does not bind one or more of EREG, BTC or TGFα. In a particular embodiment, the antibody molecule does not bind any of EREG, BTC or TGFα.

In one such embodiment, the polyspecific antibody molecule of the invention binds an antigenic fragment of AREG having the amino acid sequence shown as Sequence ID No: 1 and the antigenic fragment of HBEGF having the amino acid sequence shown as Sequence ID No: 2.

Sequence ID No: 1:
K K N P C N A E F Q N F C I H G E C K Y I E H L E
A V T C K C Q Q E Y F G E R C G E K S Sequence ID No: 2:
K R D P C L R K Y K D F C I H G E C K Y V K E L R
A P S C I C H P G Y H G E R C H As described in the Examples, antibodies raised against an antigenic fragment from this region were found to have specificity for both AREG and HB-EGF.

In one embodiment of the invention, the polyspecific, for example bispecific, antibody molecule is an antibody which shows binding specificity for HB-EGF and AREG, and for which ELISA results are shown in FIG. 9.

In one embodiment the bispecific antibody is a 4G9 antibody. In another embodiment, the antibody is a 5E4 1C8 antibody. In another embodiment, the antibody is a 5E4 2B2 antibody. In another embodiment, the antibody is an 8D6 antibody. In another embodiment, the antibody is an 8D7 antibody.

In one embodiment of the invention, polyspecific, for example bispecific, antibody is an antibody which shows binding specificity for HB-EGF and AREG, and for which ELISA results are shown in FIG. 10.

Accordingly, in one embodiment the antibody is a 4g9 2c4 1d4 antibody. In another embodiment, the antibody is a 4g9 1f5 2d5 antibody. In another embodiment, the antibody is a 4g9 1g7 2e3 antibody. In another embodiment, the antibody is an 8d7 1f6 2b10 antibody. In another embodiment, the antibody is an 8d7 1c8 2b10 antibody. In another embodiment, the antibody is an 8d7 2c2 2d7 antibody. In another embodiment, the antibody is a 4g9 1f5 1d6 antibody. In another embodiment, the antibody is a 4g9 1f5 1e11 antibody. In another embodiment, the antibody is a 4g9 1g7 1f2 antibody. In another embodiment, the antibody is a 4g9 1g7 2a3 antibody. In another embodiment, the antibody is a 4g9 2b6 1f9 antibody. In another embodiment, the antibody is an 8d7 1f6 2b3 antibody. In another embodiment, the antibody is an 8d7 1f6 2f7 antibody. In another embodiment, the antibody is an 8d7 1c8 1e9 antibody. In another embodiment, the antibody is an 8d7 1c8 1g9 antibody. In another embodiment, the antibody is an 8d7 2c2 1d11 antibody. In another embodiment, the antibody is an 8d7 2c2 1g11 antibody.

In one embodiment of the invention, polyspecific, for example bispecific, antibody is an antibody which shows binding specificity for HB-EGF and AREG, and for which ELISA results are shown in FIG. 11.

Thus in one embodiment, the antibody is an 8d6 1b7 1d9 antibody. In another embodiment, the antibody is an 8d6 1b7 1g9 antibody. In another embodiment, the antibody is an 8d61b7 2e10 antibody. In another embodiment, the antibody is an 8d61b7 2g10. In another embodiment, the antibody is an 8d6 1c7 2b6 antibody. In another embodiment, the antibody is an 8d6 1c7 2c2 antibody. In another embodiment, the antibody is an 8d6 1c7 2f9 antibody. In another embodiment, the antibody is an 8d6 1c7 2g6 antibody. In another embodiment, the antibody is an 8d6 2b4 1f6 antibody. In another embodiment, the antibody is an 8d6 2b4 1g8 antibody.

The VH and VL sequences of each of the 8d7 1c8 1e9 antibody, 8d7 1f6 2f7 antibody and 8d7 1f6 2b3 antibodies have been determined by the inventors and are as follows:

8d7 1c8 1e9 VH sequence (Sequence ID No:5):
MEWSWVILFLMAVVTGVNSEVQLQQSGAELVRPGALVKLSCKASGFNIK

DSYIHWVNQRPEQGLEWIGWIDPENGNTIYDPKFQGKASITADTSSNTA

YLQLSSLTSEDTAVYYCVSASYRYGFSYWGQGTLVTVSAAKTTPPSVYP

WVPGSLX

8d7 1c8 1e9 VL sequence (Sequence ID No: 6)
XADXISISCRSNKSLLHTNGNTYLYWFLQRPGQSPQLLIYRMSNLASGV

PDRFSGSGSGTAFTLRISRVEAEDVGVYYCMQHLEYPYTFGGGTKLEIK

RXX

8d7 1f6 2f7 VH sequence (Sequence ID No: 7):
MKCSWIIFFLMAVVTGVNSEVQLQQSGAELVRPGALVKLSCKASGFNIK

DSYIHWVNQRPEQGLEWIGWIDPENGNTIYDPKFQGKASITADTSSNTA

YLQLSSLTSEDTAVYYCVSASYRYGFSYWGQGTLVTVSAAKTTPPPVYP

LAPGSL

8d7 1f6 2f7 VL sequence (Sequence ID No: 8)
MRAPAQFLGLLVLWIPGAIGDIVMTQAAPSVPVTPGESVSISCRSNKSL

LHTNGNTYLYWFLQRPGQSPQLLIYRMSNLASGVPDRFSGSGSGTAFTL

RISRVEAEDVGVYYCMQHLEYPYTFGGGTKLEIKRADAAPTVSIFPPSS

KLG

8d7 1f6 2b3 VH sequence (Sequence ID No: 9):
MKCSWVMFFLMAVVTGVNSEVQLQQSGAELVRPGALVKLSCKASGFNIK

DSYIHWVNQRPEQGLEWIGWIDPENGNTIYDPKFQGKASITADTSSNTA

YLQLSSLTSEDTAVYYCVSASYRYGFSYWGQGTLVTVSAAKTTPPPVYP

LAPGSL

8d7 1f6 2b3 VL sequence (Sequence ID No: 10)
MRPPLSFLGLLVLWIPGAIGDIVMTQAAPSVPVTPGESVSISCRSNKSL

LHTNGNTYLYWFLQRPGQSPQLLIYRMSNLASGVPDRFSGSGSGTAFTL

RISRVEAEDVGVYYCMQHLEYPYTFGGGTKLEIKRADAAPTVSIFPPSS

KLG

In one embodiment of the invention, the antibody molecule is an antibody molecule selected from the group consisting of an antibody having the CDRS of the 8d7 1c8 1e9 antibody, an antibody having the CDRS of the 8d7 1f6 2f7 antibody, and an antibody having the CDRs of the 8d7 1f6 2b3 antibody.

The amino acid sequences of the CDRs of the antibodies may be identified using any system known in the art, for example the Rabat system (Rabat et al, Sequences of Proteins of Immunological Interest, US Dept of Health and Human Services, Public Health Service, Nat'l Inst, of Health, NIH Publication No. 91-3242, 1991 and online at www<dot>kabatdatabase<dot>com (http-immuno<dot>bme<dot>nwu<dot>edu) or the IMGT system (Brochet, X. et al., Nucl. Acids Res. 36, W503-508 (2008)).

In one embodiment, the antibody molecule comprises an antigen binding domain which comprises at least one, for example two or three of the CDRs of the VH sequence shown as Sequence ID No: 5 and/or at least one, for example two or three of the CDRs of the VL sequence shown as Sequence ID No: 6.

In another embodiment, the antibody molecule comprises an antigen binding domain which comprises at least one, for example two or three of the CDRs of the VH sequence shown as Sequence ID No: 7 and/or at least one, for example two or three of the CDRs of the VL sequence shown as Sequence ID No: 8.

In another embodiment, the antibody molecule comprises an antigen binding domain which comprises at least one, for example two or three of the CDRs of the VH sequence shown as Sequence ID No: 9 and/or at least one, for example two or three of the CDRs of the VL sequence shown as Sequence ID No: 10.

In a particular embodiment, the antibody molecule comprises an antigen binding domain comprising all three of the CDRs of the VH sequence shown as Sequence ID No: 5 and/or all three of the CDRs of the group consisting of the VH sequence shown as Sequence ID No: 6

In a particular embodiment, the antibody molecule comprises an antigen binding domain comprising all three of the CDRs of the VH sequence shown as Sequence ID No: 7 and/or all three of the CDRs of the group consisting of the VH sequence shown as Sequence ID No: 8

In a particular embodiment, the antibody molecule comprises an antigen binding domain comprising all three of the CDRs of the VH sequence shown as Sequence ID No: 9 and/or all three of the CDRs of the group consisting of the VH sequence shown as Sequence ID No: 10

In a particular embodiment, the antibody molecule comprises the VH domain shown as Sequence ID No: 5 and/or the VL sequence shown as Sequence ID No: 6.

In a particular embodiment, the antibody molecule comprises the VH domain shown as Sequence ID No: 7 and/or the VL sequence shown as Sequence ID No: 8.

In a particular embodiment, the antibody molecule comprises the VH domain shown as Sequence ID No: 9 and/or the VL sequence shown as Sequence ID No: 10.

In a second aspect of the invention, there is provided a nucleic acid molecule which encodes a polyspecific antibody molecule according to the first aspect of the invention.

In one embodiment, the antibody molecule has an affinity for its target of at least $10^{-7}$ M, for example at least $10^{-8}$ M, or higher e.g. 10 9 M, or higher for each of its targets for which it has specificity.

The antibody molecules or nucleic acid molecules of the invention may be used as therapeutic agents or may be used as diagnostic agents, either in vivo, in vitro, or ex vivo.

Accordingly, in a third aspect of the invention, there is provided a polyspecific antibody molecule according to the first aspect of the invention or a nucleic acid molecule according to the second aspect of the invention for use in medicine.

In one embodiment, the polyspecific antibody molecule may be used in the treatment of a disease or disorder associated with angiogenesis. Such conditions include neoplastic disease, various inflammatory disorders, tumours, various autoimmune disorders, some hereditary disorders, and ocular disorders.

Thus, a fourth aspect of the invention, provides a polyspecific antibody molecule according to the first aspect of the invention or a nucleic acid molecule according to the second aspect of the invention for use in the treatment of an angiogenesis associated disease.

Also encompassed within the fourth aspect of the invention is the use of a polyspecific antibody molecule according to the first aspect of the invention or a nucleic acid molecule according to the second aspect of the invention in the preparation of a medicament for the treatment of an angiogenesis associated disease.

In a fifth aspect, the invention provides a method of treating angiogenesis associated disease in a subject, said method comprising administration to said subject of an effective amount of the polyspecific antibody according to the first aspect of the invention or a nucleic acid molecule according to the second aspect of the invention.

In a particular embodiment of the invention, the antibodies and nucleic acids are used to treat neoplastic disease.

Thus in a sixth aspect, there is provided a polyspecific antibody according to the first aspect of the invention or a nucleic acid molecule according to the second aspect of the invention for use in the treatment of neoplastic disease.

Also encompassed within the sixth aspect of the invention is the use of a polyspecific antibody molecule according to the first aspect of the invention or a nucleic acid molecule according to the second aspect of the invention in the preparation of a medicament for the treatment of neoplastic disease.

In a seventh aspect, the invention provides a method of treating neoplastic disease in a subject, said method comprising administration to said subject of an effective amount of the polyspecific antibody according to the first aspect of the invention or a nucleic acid molecule according to the second aspect of the invention.

The methods of the invention may be used to treat any neoplastic disease. In a particular embodiment, the neoplastic disease is cancer. For example, neoplastic diseases which may be treated using the antibodies, nucleic acids, compositions and methods of the invention include, but are not limited to, colorectal cancer, breast cancer, lung cancer, prostate cancer, hepatocellular cancer, lymphoma, leukaemia, gastric cancer, pancreatic cancer, cervical cancer, ovarian cancer, liver cancer, renal cancer, thyroid cancer, melanoma, carcinoma, head and neck cancer, and skin cancer.

In one particular embodiment, the neoplastic disease is colorectal cancer.

In another embodiment, the neoplastic disease is breast cancer.

In another embodiment, the neoplastic disease is lung cancer.

The inventors have shown that certain EGFs are upregulated by chemotherapies in p53 mutant tumour cells as well as in p53 wild type tumours. This is particularly surprising given that resistance to chemotherapy has previously been shown to be largely dependent on p53 status. Accordingly, in a particular embodiment, the neoplastic disease is a cancer comprising a p53 mutation.

An eighth aspect of the invention provides a pharmaceutical composition comprising a polyspecific antibody molecule according the first aspect of the invention or a nucleic acid molecule according to the second aspect of the invention.

The antibody molecules of the invention, or indeed nucleic acid molecules encoding said antibody molecules, may be used as sole therapy in treating neoplastic disease. However, as noted herein, the inventors have demonstrated that combinations of EGF inhibitors with various chemotherapies attenuate tumour cell growth to an extent greater than could be predicted from the effects of each inhibitor alone.

Accordingly, in one embodiment, the antibody molecules of the invention or nucleic acid molecules encoding said antibody molecules are contemplated for use in combination treatment regimens with other active agents, for example chemotherapeutic agents and/or antiangiogenic agents.

Thus, in one aspect of the invention, the antibody molecule, or nucleic acid molecule, may be used in a treatment regimen simultaneously, separately or sequentially with a chemotherapeutic agent and/or an anti-angiogenic agent.

Chemotherapeutic agents which may be used with the antibody molecules of the invention include, but are not limited to, antimetabolites, topoisomerase inhibitors, alkylating agents, anthracyclines, and plant alkaloids.

In one embodiment, the chemotherapeutic agent is a topoisomerase I inhibitor. In these aspects of the invention, any topisomerase inhibitor may be used. In a particular embodiment, the topoisomerase inhibitor is CPT-11. In another embodiment, the topoisomerase inhibitor is an active metabolite of CPT-11, for example SN-38.

In one embodiment, combination therapy employing an antibody molecule of the invention and an agent which inhibits angiogenesis, for example by inhibiting vascular endothelial growth factor (VEGF), may be used.

Any suitable angiogenesis inhibitor may be used in the invention. However, in a particular embodiment, the angiogenesis inhibitor is selected from the group consisting of Sorafenib Bayer/onyx), Sunitinib (Pfizer), PTK787 (Novartis), AG013676 (Pfizer), ZD6474 (AstraZeneca) and VEGF-Trap (Regeneron), AG-13958 (Pfizer), VEGF siRNA such as Cand5, squalamine (Evizon™), anecortave (Retaane™), and Combretastatin.

In particular embodiments, combination therapy including at least an antibody molecule of the invention and two, three, or more agents in combination may be used. For example combinations including a chemotherapeutic agent and an antiangiogenesis agent may be used.

As described above, in one embodiment of the invention, the polyspecific antibody has binding specificity for AREG and, in addition, binding specificity for at least one further EGF. In one such embodiment, an antibody molecule which may be used has a first heavy chain and a first light chain from the antibody 6E11 1E9 106 and an additional antibody heavy chain and light chain with binding specificity for a second EGF, wherein the heavy chain and first light chain do not bind said second EGF.

The VH and VL sequences of the 6E11 1E9 106 antibody have been determined by the inventors and are as follows.

```
6E11 1E9 1C6 VH sequence (Sequence ID No: 3):
MECNWILPFILSVTSGVYSQVQLQQSGAELARPGASVKLSCKASGYTFT

RYWMQWIKQRPGQGLEWIGAIYPGNGDIRYTQKFKGKATLTADKSSSTA

YMQLSSLASEDSAVYYCARGTTPSSYWGQGTLVTVSAAKTTAPSVYPLA

PVCGDTTGSSVTLGCLVKGYF

6E11 1E9 1C6 VL sequence (Sequence ID No: 4)
MMSPAQFLFLLVLWIRETSGDVVMTQTPLTLSVSIGQPASISCKSSQSL

LDSDGKTYLNWLLQRPGQSPKRLIYLVSKLDSGVPDRFTGSGSGTDFTL

KISRVEAEDLGVYYCWQGTHFPWTFGGGTKLEIKRADAAPTVSIFPPSS

EQLTSGGASVVCFLNNFYPK
```

In one embodiment of the invention the antibody molecule having binding specificity for AREG and a second EGF of and for use in the invention is an antibody molecule comprising at least one of the CDRs of the 6E11 1E9 106 VH region and/or at least one of the CDRs of the 6E11 1E9 106 VL region and having CDRs with binding specificity for a second EGF.

The antibody molecules of the invention may be used in assays, for example diagnostic assays.

Thus, in a ninth aspect, the invention provides a method of identifying the presence of one or more EGFs in a cell, said method comprising bringing said cell into contact with antibody molecules of the first aspect of the invention and determining binding between said antibody molecules and said cell.

The demonstration by the present inventors that expression of EGFs are upregulated in response to treatment with various chemotherapies, for example topoisomerase inhibitors, suggests that the therapeutic effect of treatment with these chemotherapies may, in certain patients, be compromised by the upregulation of EGFs.

Thus, the invention may be used in assays to determine whether or not treatment with a chemotherapeutic agent may be effective in a particular patient.

Thus, in an tenth aspect of the present invention, there is provided an in vitro method for evaluating the response of tumour cells from a subject to the presence of a chemotherapeutic agent to predict response of the tumour cells in vivo to treatment with the chemotherapeutic agent, which method comprises:
(a) providing a sample of tumour cells from a subject exposed to said chemotherapeutic agent;
(b) exposing a portion of said sample of tumour cells to antibody molecules of the invention;
(c) comparing binding of the antibody molecules to that on a control portion of said sample which has not been exposed to said chemotherapeutic agent; wherein enhanced binding in the portion of sample exposed to said chemotherapeutic agent is indicative of decreased sensitivity to said chemotherapeutic agent.

The invention further represents a tool for prognosis and diagnosis of a subject afflicted with a tumour. For the purpose of prognosis, determining the expression level of EGFs before and after chemotherapeutic treatment can be used to identify if the subject will respond to a combinatory treatment approach. For the purpose of diagnosis the cell surface expression profile of EGFs of a tumour in response to chemotherapy can be used to identify which combination therapy would be most effective for that tumour.

Thus, an eleventh aspect of the invention provides a method of prognosis for evaluating the response of a patient to combination therapy comprising a chemotherapeutic agent and an EGF inhibitor, for example an antibody molecule of the invention, said method comprising (a) determining binding of an antibody molecule of the invention to EGFs in an in vitro sample containing tumour cells obtained from a subject prior to treatment with said chemotherapeutic treatment
(b) determining binding of said antibody molecules to said EGFs in an in vitro sample containing tumour cells obtained from a subject after treatment with said chemotherapeutic treatment;
(c) comparing binding in (b) with binding in (a), wherein enhanced binding in (b) compared to (a) is indicative that the patient may benefit from combination therapy comprising a chemotherapeutic agent and an inhibitor of said EGF.

By using the polyspecific antibodies of the invention, the expression of two or more EGFs may be assayed using a single population of identical antibodies.

In an embodiment of the invention, binding of an antibody molecule to an EGF in the sample exposed to said chemotherapeutic agent is considered to be enhanced if the binding is at least 1.5-fold, preferably at least 2-fold, more preferably at least 5-fold, that of binding to EGFs in the control portion of said sample which has not been exposed to said chemotherapeutic agent.

In the present application, unless the context demands otherwise, where reference is made to a chemotherapeutic agent and/or antiangiogenesis agent and an EGF modulator, for example an antibody molecule of the first aspect of the invention, the chemotherapeutic agent, the antiangiogenesis agent and the EGF modulator are different agents. Generally, the chemotherapeutic agent, the antiangiogenesis agent and the EGF modulator will have a different mode of action from the EGF modulator. In one embodiment, the chemotherapeutic agent will not inhibit the EGF.

Preferred and alternative features of each aspect of the invention are as for each of the other aspects mutatis mutandis unless the context demands otherwise.

DETAILED DESCRIPTION

The present invention is based on the demonstration that particular combinations of two or more EGF inhibitors demonstrate superadditive effects in the attenuation of tumour cell growth and, moreover, that polyspecific antibodies having binding specificity for two or more EGFs may be used to efficiently bind EGFs and may be used in diagnostic and therapeutic methods.

Assays

As described above, in one embodiment, the present invention relates to methods of screening samples comprising tumour cells for expression of EGF genes or polypeptides, for example, in order to determine suitability for treatment using particular chemotherapeutic agents.

The EGF-family of peptide growth factors is made up of 10 members which have the ability to selectively bind the ErrB receptors (ErrB1 or EGF receptor, ErrB2 or Her2, ErrB3 and ErrB4).

In one embodiment of the invention, the EGF is a ligand of ErbB-1, for example, amphiregulin (AREG), TGF, Epiregulin (EREG) or BTC.

In another embodiment, the EGF is a ligand of ErbB-4, for example NRG3

Accession details are provided for each of these genes below.

| Gene | Accession No |
| --- | --- |
| BTC | NM_001729 |
| HB-EGF: | NM_001945 |
| AREG | NM_001657 |
| TGFA | NM_003236 |
| EREG | NM_001432 |
| NRG3 | NM_001010848 |

The expression of any gene encoding an EGF of interest may be determined.

For example, where the EGF is AREG, the Areg gene may be NM_001657.

In a particular embodiment of the invention, the polyspecific antibody molecule for use in the invention has specificity for AREG and for HB-EGF. An example of a gene encoding AREG has accession no: NM_001657. An example of a gene encoding HB-EGF has accession no: NM_001945.

In one embodiment, assays of the invention may be used to monitor disease progression, for example using biopsy samples at different times. In such embodiments, instead of comparing binding to a expression of EGF against a control sample which has not been exposed to said chemotherapeutic agent, the expression of the EGF may be compared against a sample obtained from the same tissue at an earlier time point, for example from days, weeks or months earlier.

The methods of the invention may be used to determine the suitability for treatment of any suitable cancer with a chemotherapeutic agent e.g. CPT-11 or analogues thereof. For example the methods of the invention may be used to determine the sensitivity or resistance to treatment of cancers including, but not limited to, gastrointestinal, such as colorectal, head and neck cancers.

In a particular embodiment of the invention, the methods of the invention may be used to determine the sensitivity or resistance to treatment of colorectal cancer.

In another particular embodiment of the invention, the methods of the invention may be used to determine the sensitivity or resistance to treatment of lung cancer.

In another particular embodiment of the invention, the methods of the invention may be used to determine the sensitivity or resistance to treatment of breast cancer.

The nature of the tumour or cancer will determine the nature of the sample which is to be used in the methods of the invention. The sample may be, for example, a sample from a tumour tissue biopsy, bone marrow biopsy or circulating tumour cells in e.g. blood. Alternatively, e.g. where the tumour is a gastrointestinal tumour, tumour cells may be isolated from faeces samples. Other sources of tumour cells may include plasma, serum, cerebrospinal fluid, urine, interstitial fluid, ascites fluid etc. For example, solid tumour samples may be collected in complete tissue culture medium with antibiotics. Cells may be manually teased from the tumour specimen or, where necessary, enzymatically disaggregated by incubation with collagenase/DNAse and suspended in appropriate media containing, for example, human or animal sera.

In other embodiments, biopsy samples may be isolated and frozen or fixed in fixatives such as formalin. The samples may then be tested for expression levels of genes at a later stage.

In determining treatment, it may be desirable to determine p53 status of a cancer. For example, p53 status may be useful as it may dictate the type of chemotherapy which should be used in combination with particular EGF proteins. p53 status may be determined using conventional methods. For example, the use of immunohistochemistry may be used to identify hotspot mutations while gene sequencing or other DNA analysis methodologies may also be employed. This analysis may suitably be performed on isolated tumour tissue.

Antibody Molecules

As described above, the invention provides a polyspecific antibody molecule which binds at least two, such as three or four, different EGF molecules. In one embodiment, the antibody specifically binds two, three or four of the EGFs selected from HB-EGF, AREG, EREG, BTC or TGFα.

Such polyspecific antibodies may be generated using any known method in the art. A number of methods are known in the art for the production of antibody polyspecific, for example bispecific, antibodies and fragments. For example, such methods include the fusion of hybridomas or linking of Fab' fragments (for example, see Songsivilai & Lachmann, Clin. Exp. Immunol. 79: 315-321 (1990), Kostelny et al., J. Immunol. 148:1547-1553 (1992)). In another embodiment, bispecific antibodies may be formed as "diabodies".

In an alternative strategy developed by the inventors, an antigen is produced which corresponds to an immune dominant conserved region of the antigens to which it is desired to produce a polyspecific antibody, and monoclonal antibodies are then raised to said region. By employing this technique, antibodies with multiple specificities can be made without the need for engineering.

In one embodiment, the antigen comprises, for example consists of, a polypeptide having an amino acid sequence having at least 70%, such as at least 80%, at least 90% or at least 95% sequence identity with corresponding sequences in each of the EGFs to which it binds.

Sequence identity or "homology" may be determined using any suitable method known in the art. For example, sequence identity may be determined using computer programs such as the BLAST, DOMAIN, BEAUTY (BLAST Enhanced Alignment Utility), GENPEPT and TREMBL packages. An additional means of determining homology is via determination of sequence hybridization, methods of which are well described in the art (See, for example, "Nucleic Acid Hybridization" Hames, B. D., and Higgins S. J., Eds. (1985); Sambrook et al., 1989, Molecular Cloning, A Laboratory Manual, (Volumes 1-3) Cold Spring Harbor Press, N.Y.; and Ausubel et al., 1989, Current Protocols in Molecular Biology, Green Publishing Associates and Wiley Interscience, N.Y).

The strategy for developing a bispecific antibody employed by the inventors is not limited to development of polyspecific antibodies with binding specificities for two or more EGFs but may be employed in the development of polyspecific antibodies to other antigens against which a polyspecific antibody may be useful.

Accordingly, in an independent aspect of the invention, there is provided a method of producing a polyspecific, for example bispecific, antibody against two or more targets, e.g. polypeptides, said method comprising the steps:

identifying a putative antigenic region consisting of a region of homology between the amino acid sequences of said two or more targets;

producing a recombinant protein comprising said putative antigenic region;

raising monoclonal antibodies against said recombinant protein; and optionally, testing the specificity of the monoclonal antibodies against said targets and said recombinant protein.

In one embodiment, the recombinant protein does not comprise antigenic amino acid sequences which are present in one of said targets but not present on the other target(s).

In one embodiment of the invention, the polyspecific antibody is a bispecific antibody having specificity for AREG and HBEGF. In one such embodiment, the bispecific antibody molecule of the invention binds an antigenic fragment of AREG having the amino acid sequence shown as Sequence ID No: 1 and the antigenic fragment of HBEGF having the amino acid sequence shown as Sequence ID No: 2.

```
Sequence ID No: 1:
K K N P C N A E F Q N F C I H G E C K Y I E H L E
A V T C K C Q Q E Y F G E R C G E K S Sequence ID No: 2:
K R D P C L R K Y K D F C I H G E C K Y V K E L R
A P S C I C H P G Y H G E R C H
```

Particular examples of antibodies developed in this way and for which the VH and VL sequences are described above are the 8d7 1c8 1e9 antibody, the 8d7 1f6 2f7 antibody, and the 8d7 1f6 2b3 antibody.

In another embodiment, a bispecific antibody molecule for use in the present invention may comprise a first heavy chain and a first light chain from the antibody 6E11 1E9 106, which has binding specificity for AREG and an additional antibody heavy chain and light chain with binding specificity for HB-EGF. In one embodiment, the heavy chain and light chain have binding specificity for a region of HB-EGF which is involved in binding to an EGF receptor. In another embodiment, the heavy chain and light chain have binding specificity for a region of HB-EGF which is not involved in binding to an EGF receptor.

Fragments of antibodies may retain the binding ability of the intact antibody and may be used in place of the intact antibody. Accordingly, for the purposes of the present invention, unless the context demands otherwise, the term "antibody molecules" should be understood to encompass antibody fragments. Examples of antibody fragments include Fab, Fab', F (ab')$_2$, Fd, dAb, and Fv fragments, scFvs, bispecific scFvs, diabodies, linear antibodies (see U.S. Pat. No. 5,641,870, Example 2; Zapata et al., Protein Eng 8 (10): 1057-1062 [1995]); single-chain antibody molecules; and multispecific antibodies formed from antibody fragments.

The Fab fragment consists of an entire L chain (VL and CL), together with VH and CH1. Fab' fragments differ from Fab fragments by having additional few residues at the carboxy terminus of the CH1 domain including one or more cysteines from the antibody hinge region. The F (ab') 2 fragment comprises two disulfide linked Fab fragments.

Fd fragments consist of the VH and CH1 domains.

Fv fragments consist of the VL and VH domains of a single antibody.

Single-chain Fv fragments are antibody fragments that comprise the VH and VL domains connected by a linker which enables the scFv to form an antigen binding site. (see Pluckthun in The Pharmacology of Monoclonal Antibodies, vol. 113, Rosenburg and Moore eds., Springer-Verlag, New York, pp. 269-315 (1994).

Diabodies are small antibody fragments prepared by constructing scFv fragments (see preceding paragraph) with short linkers (about 5-10 residues) between the VH and VL domains such that inter-chain but not intra-chain pairing of the V domains is achieved, resulting in a multivalent fragment, i.e. a fragment having two antigen-binding sites (see, for example, EP 404 097; WO 93/11161; and Hollinger et al., Proc. Natl. Acad. Sci. USA, 90: 6444-6448 (1993))

Further encompassed by fragments are individual CDRs.

In the present invention, polyspecific antibodies which bind two or more EGFs have been developed.

As described above, the antibody molecules of the present invention are not limited to antibody molecules having VH, VL and the CDRs having the amino acid sequences of said antibody molecules but also extends to variants thereof which maintain the ability to inhibit the specifically bind two, three or four EGF molecules. Thus, for example, the CDR amino acid sequences of such antibody molecules, for example the antibody molecules identified in FIG. 9, 10 or 11 of the application, in which one or more amino acid residues are modified may also be used as the CDR sequence. Modified amino acid residues in the amino acid sequences of the CDR variant are preferably 30% or less, more preferably 20% or less, most preferably 10% or less, within the entire CDR. Such variants may be provided using the teaching of the present application and techniques known in the art. The CDRs may be carried in a framework structure comprising an antibody heavy or light chain sequence or part thereof. Preferably such CDRs are positioned in a location corresponding to the position of the CDR(s) of naturally occurring VH and VL domains. The positions of such CDRs may be determined as described in Kabat et al, Sequences of Proteins of Immunological Interest, US Dept of Health and Human Services, Public Health Service, Nat'l Inst, of Health, NIH Publication No. 91-3242, 1991 and online at www<dot>kabatdatabase<dot>com http-immuno<dot>bme<dot>nwu<dot>edu.

Furthermore, modifications may alternatively or additionally be made to the Framework Regions of the variable regions. Such changes in the framework regions may improve stability and reduce immunogenicity of the antibody.

Antibody molecules of or for use in the invention herein include antibody fragments and "chimeric" antibodies in which a portion of the heavy and/or light chain is identical with or homologous to corresponding sequences in antibodies derived from a particular species or belonging to a particular antibody class or subclass, while the remainder of the chain (s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81: 6851-6855 (1984)). Chimeric antibodies of interest herein include "primatized" antibodies comprising variable domain antigen-binding sequences derived from a non-human primate (e.g. Old World Monkey, Ape etc), and human constant region sequences.

Antibody molecules, such as antibodies and antibody fragments, for use in the present invention may be produced in any suitable way, either naturally or synthetically. Such methods may include, for example, traditional hybridoma techniques (Kohler and Milstein (1975) Nature, 256:495-499), recombinant DNA techniques (see e.g. U.S. Pat. No. 4,816,567), or phage display techniques using antibody libraries (see e.g. Clackson et al. (1991) Nature, 352: 624-628 and Marks et al. (1992) Bio/Technology, 10: 779-783). Other antibody production techniques are described in Using Antibodies: A Laboratory Manual, eds. Harlow and Lane, Cold Spring Harbor Laboratory, 1999.

Traditional hybridoma techniques typically involve the immunisation of a mouse or other animal with an antigen in order to elicit production of lymphocytes capable of binding the antigen. The lymphocytes are isolated and fused with a myeloma cell line to form hybridoma cells which are then cultured in conditions which inhibit the growth of the parental myeloma cells but allow growth of the antibody producing cells. The hybridoma may be subject to genetic mutation, which may or may not alter the binding specificity of antibodies produced. Synthetic antibodies can be made using techniques known in the art (see, for example, Knappik et al, J. Mol. Biol. (2000) 296, 57-86 and Krebs et al, J. Immunol. Meth. (2001) 2154 67-84.

Modifications may be made in the VH, VL or CDRs of the antibody molecules, or indeed in the FRs using any suitable technique known in the art. For example, variable VH and/or VL domains may be produced by introducing a CDR, e.g. CDR3 into a VH or VL domain lacking such a CDR. Marks et al. (1992) Bio/Technology, 10: 779-783 describe a shuffling technique in which a repertoire of VH variable domains lacking CDR3 is generated and is then combined with a CDR3 of a particular antibody to produce novel VH regions. Using analogous techniques, novel VH and VL domains comprising CDR derived sequences of the present invention may be produced.

Alternative techniques of producing antibodies for use in the invention may involve random mutagenesis of gene(s) encoding the VH or VL domain using, for example, error prone PCR (see Gram et al, 1992, P.N.A.S. 89 3576-3580. Additionally or alternatively, CDRs may be targeted for mutagenesis e.g. using the molecular evolution approaches described by Barbas et al 1991 PNAS 3809-3813 and Scier 1996 J Mol Biol 263 551-567.

An antibody for use in the invention may be a "naked" antibody (or fragment thereof) i.e. an antibody (or fragment thereof) which is not conjugated with an "active therapeutic agent". An "active therapeutic agent" is a molecule or atom which is conjugated to a antibody moiety (including antibody fragments, CDRs etc) to produce a conjugate. Examples of such "active therapeutic agents" include drugs, toxins, radio-isotopes, immunomodulators, chelators, boron compounds, dyes etc.

An antibody molecule for use in the invention may be in the form of an immunoconjugate, comprising an antibody fragment conjugated to an "active therapeutic agent". The therapeutic agent may be a chemotherapeutic agent or another molecule.

Methods of producing immunoconjugates are well known in the art; for example, see U.S. Pat. No. 5,057,313, Shih et al., Int. J. Cancer 41: 832-839 (1988); Shih et al., Int. J. Cancer 46: 1101-1106 (1990), Wong, Chemistry Of Protein Conjugation And Cross-Linking (CRC Press 1991); Upeslacis et al., "Modification of Antibodies by Chemical Methods," in Monoclonal Antibodies: Principles And Applications, Birch et al. (eds.), pages 187-230 (Wiley-Liss, Inc. 1995); Price, "Production and Characterization of Synthetic Peptide-Derived Antibodies," in Monoclonal Antibodies: Production, Engineering And Clinical Application, Ritter et al. (eds.), pages 60-84 (Cambridge University Press 1995).

The antibody molecules of and for use in the invention may comprise further modifications. For example the antibody molecules can be glycosylated, pegylated, or linked to albumin or a nonproteinaceous polymer.

Chemotherapeutic Agents

As described above, in certain embodiments of the invention the antibody molecules may be used in combination with chemotherapeutic agents. For example chemotherapeutic agents which may be used include antimetabolites, including thymidylate synthase inhibitors, nucleoside analogs, platinum cytotoxic agents, topoisomerase inhibitors or antimicrotubules agents. Examples of thymidylate synthase inhibitors which may be used in the invention include 5-FU, MTA and TDX. An example of an antimetabolite which may be used is tomudex (TDX). Examples of platinum cytotoxic agents which may be used include cisplatin and oxaliplatin.

Chemotherapeutic agents which may be used in the present invention, in addition or instead of the specific agents recited above, may include alkylating agents; alkyl sulfonates; aziridines; ethylenimines; methylamelamines; nitrogen mustards; nitrosureas; anti-metabolites; folic acid analogues; purine analogs; pyrimidine analogs; androgens; anti-adrenals; folic acid replenishers; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; ionidamine; mitoguazone; and mitoxantrone.

In particular embodiments of the invention, the chemotherapeutic agent is a topoisomerase inhibitor. Any suitable topoisomerase inhibitor may be used in the present invention. In a particular embodiment, the topoisomerase inhibitor is a topoisomerase I inhibitor, for example a camptothecin. A suitable topoisomerase I inhibitor, which may be used in the present invention is irinotecan (CPT-11) or its active metabolite SN-38. CPT-11 specifically acts in the S phase of the cell cycle by stabilizing a reversible covalent reaction intermediate, referred to as a cleavage or cleavage complex, and may also induce $G_2$-M cell cycle arrest.

In certain embodiments of the invention, the chemotherapeutic agent is a fluoropyrimidine e.g. 5-FU.

Where reference is made to specific chemotherapeutic agents, it should be understood that analogues including biologically active derivatives and substantial equivalents thereof, which retain the antitumour activity of the specific agents, may be used.

In the present application, unless the context demands otherwise, where reference is made to a chemotherapeutic agent and an EGF modulator, for example an antibody molecule of the first aspect of the invention, the chemotherapeutic agent and the EGF modulator are different agents. Generally, the chemotherapeutic agent will have a different mode of action from the EGF modulator. In one embodiment, the chemotherapeutic agent will not inhibit the EGF.

Treatment with the polyspecific antibodies of the invention may additionally or alternatively be combined with treatment using one or more EGF inhibitors other than an antibody. Suitable inhibitors may include Tyrphostin AG 1478 (a selective and potent inhibitor of EGF-R kinase) which indirectly inhibits TGF-alpha; and ZM 252868, an Epidermal growth factor (EGF) receptor-specific tyrosine kinase inhibitor which inhibits TGF-alpha actions in ovarian cancer cells (Simpson et al, British Journal of Cancer, 79(7-8):1098-103, 1999).

A suitable inhibitor of HB-EGF may include CRM197.

In another embodiment, a nucleic acid modulator which inhibits expression of an EGF, may be used. Such nucleic acid modulators may include, but are not limited to antisense molecules, short interfering nucleic acid (siNA), for example short interfering RNA (siRNA), double-stranded RNA (dsRNA), micro RNA, short hairpin RNA (shRNA), nucleic acid sensor molecules, allozymes, enzymatic nucleic acid molecules, and triplex oligonucleotides and any other nucleic acid molecule which can be used in mediating RNA interference "RNAi" or gene silencing in a sequence-specific manner (see for example Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914; Allshire, 2002, Science, 297, 1818-1819; Volpe et al., 2002, Science, 297, 1833-1837; Jenuwein, 2002, Science, 297, 2215-2218; Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831).

An "antisense nucleic acid", is a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). The antisense molecule may be complementary to a target sequence along a single contiguous sequence of the antisense molecule or may, in certain embodiments, bind to a substrate such that the substrate, the antisense molecule or both can bind such that the antisense molecule forms a loop such that the antisense molecule can be complementary to two or more non-contiguous substrate sequences or two or more non-contiguous sequence portions of an antisense molecule can be complementary to a target sequence, or both. Details of antisense methodology are known in the art, for example see Schmajuk et al., 1999, J. Biol. Chem., 274, 21783-21789, Delihas et al., 1997, Nature, 15, 751-753, Stein et al., 1997, Antisense N. A. Drug Dev., 7, 151, Crooke, 2000, Methods Enzymol., 313, 3-45; Crooke, 1998, Biotech. Genet. Eng. Rev., 15, 121-157, Crooke, 1997, Ad. Pharmacol., 40, 1-49.

A "triplex nucleic acid" or "triplex oligonucleotide" is a polynucleotide or oligonucleotide that can bind to a double-stranded DNA in a sequence-specific manner to form a triple-strand helix. Formation of such triple helix structure has been shown to modulate transcription of the targeted gene (Duval-Valentin et al., 1992, Proc. Natl. Acad. Sci. USA, 89, 504).

Aptamers are nucleic acid (DNA and RNA) macromolecules that bind tightly to a specific molecular target. They can be produced rapidly through repeated rounds of in vitro selection for example by SELEX (systematic evolution of ligands by exponential enrichment) to bind to various molecular targets such as small molecules, proteins, nucleic acids etc (see Ellington and Szostak, Nature 346(6287):818-822 (1990), Tuerk and Gold, Science 249(4968):505-510 (1990) U.S. Pat. No. 6,867,289; U.S. Pat. No. 5,567,588, U.S. Pat. No. 6,699,843).

In addition to exhibiting remarkable specificity, aptamers generally bind their targets with very high affinity; the majority of anti-protein aptamers have equilibrium dissociation constants (Kds) in the picomolar (pM) to low nanomolar (nM) range. Aptamers are readily produced by chemical synthesis, possess desirable storage properties, and elicit little or no immunogenicity in therapeutic applications.

Non-modified aptamers are cleared rapidly from the bloodstream, with a half-life of minutes to hours, mainly due to nuclease degradation and renal clearance, a result of the aptamer's inherently low molecular weight. However, as is known in the art, modifications, such as 2'-fluorine-substituted pyrimidines, polyethylene glycol (PEG) linkage, etc. can be used to adjust the half-life of the molecules to days or weeks as required.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range). The variable loop length is typically comprised of 10 to 20 amino acids, and the scaffold may be any protein which has good solubility and compacity properties. Aptamers may comprise any deoxyribonucleotide or ribonucleotide or modifications of these bases, such as deoxythiophosphate (or phosphorothioate), which have sulfur in place of oxygen as one of the non-bridging ligands bound to the phosphorus. Monothiophosphates αS have one sulfur atom and are thus chiral around the phosphorus center. Dithiophosphates are substituted at both oxygens and are thus achiral. Phosphorothioate nucleotides are commercially available or can be synthesized by several different methods known in the art.

Treatment

"Treatment" or "therapy" includes any regime that can benefit a human or non-human animal. The treatment may be in respect of an existing condition or may be prophylactic (preventative treatment). Treatment may include curative, alleviation or prophylactic effects.

The antibody molecules, nucleic acids and compositions of the invention may be used in the treatment of other disorders mediated by or associated with angiogenesis. Such conditions include, various inflammatory disorders, tumours, various autoimmune disorders, some hereditary disorders, and ocular disorders.

The antibody molecules and methods of the invention may be used in the treatment of angiogenesis associated inflammation, including various forms of arthritis, such as rheumatoid arthritis and osteoarthritis, chronic inflammatory conditions including ulcerative colitis, Crohn's disease, bartonellosis, and atherosclerosis.

Other angiogenesis-mediated disorders, for which the invention may be used include hemangioma, solid tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, retrolental fibroplasia, arthritis, diabetic neovascularization, peptic ulcer, Helicobacter related diseases, fractures, keloids, and vasculogenesis.

Ocular Disorders mediated by angiogenesis for which the invention may be used to treat include macular degeneration, ocular neovascular disease corneal graft rejection, neovascularization following injury or infection, rubeosis, diabetic retinopathy, retrolental fibroplasia and neovascular glaucoma, corneal diseases and macular degeneration, diabetic retinopathy, retinopathy of prematurity, corneal graft rejection, neovascular glaucoma and retrolental fibroplasia, diseases associated with corneal neovascularization including, but are not limited to, epidemic keratoconjunctivitis, Vitamin A deficiency, atopic keratitis, superior limbic keratitis, pterygium keratitis sicca, and periphigoid radial keratotomy, diseases associated with retinal/choroidal neovascularization including, but are not limited to, macular degeneration, presumed myopia, optic pits, chronic retinal detachment, hyperviscosity syndromes, trauma and post laser complications, diseases associated with rubeosis (neovascularization of the angle) and diseases caused by the abnormal proliferation of fibrovascular or fibrous tissue including all forms of proliferative vitreoretinopathy, neovascular glaucoma, retinoblastoma, retrolental fibroplasia, rubeosis, uveitis, and corneal graft neovascularization other eye inflammatory diseases, ocular tumors, and diseases associated with iris neovascularization.

"Treatment of neoplastic disease or cancer" includes treatment of conditions caused by cancerous growth and/or vascularisation and includes the treatment of neoplastic growths or tumours. Examples of tumours that can be treated using the invention are, for instance, sarcomas, including osteogenic and soft tissue sarcomas, carcinomas, e.g., breast-, lung-, bladder-, thyroid-, prostate-, colon-, rectum-, pancreas-, stomach-, liver-, uterine-, prostate, cervical and ovarian carcinoma, non-small cell lung cancer, hepatocellular carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, astrocytomas, gliomas and retinoblastomas.

The invention may be particularly useful in the treatment of existing cancer and in the prevention of the recurrence of cancer after initial treatment or surgery.

Pharmaceutical Compositions

Pharmaceutical compositions according to the present invention, and for use in accordance with the present invention may comprise, in addition to active ingredients, e.g. polyspecific antibody molecules, and/or nucleic acid molecules encoding such antibody molecules, a pharmaceutically acceptable excipient, a carrier, buffer, stabiliser or other materials well known to those skilled in the art (see, for example, Remington: the Science and Practice of Pharmacy, $21^{st}$ edition, Gennaro A R, et al, eds., Lippincott Williams & Wilkins, 2005.). Such materials may include buffers such as acetate, Tris, phosphate, citrate, and other organic acids; antioxidants; preservatives; proteins, such as serum albumin, gelatin, or immunoglobulins; hydrophilic polymers such aspolyvinylpyrrolidone; amino acids such as glycine, glutamine, asparagine, histidine, arginine, or lysine; carbohydrates; chelating agents; tonicifiers; and surfactants.

The pharmaceutical compositions may also contain one or more further active compounds selected as necessary for the particular indication being treated, preferably with complementary activities that do not adversely affect the activity of the composition of the invention. For example, in the treatment of cancer, in addition to polyspecific antibody molecules, the formulation or kit may comprise an additional component, for example an antibody to a target other than the EGF to which the antibody molecules bind, for example to a growth factor which affects the growth of a particular cancer.

The active ingredients may be administered via microspheres, microcapsules, liposomes, other microparticulate delivery systems. For example, active ingredients may be entrapped within microcapsules which may be prepared, for example, by coacervation techniques or by interfacial polymerization, for example, hydroxymethylcellulose or gelatine microcapsules and poly-(methylmethacylate) microcapsules, respectively, in colloidal drug delivery systems (for example, liposomes, albumin microspheres, macroemulsions, nanoparticles and nanocapsules) or in macroemulsions. For further details, see Remington: the Science and Practice of Pharmacy, $21^{St}$ edition, Gennaro A R, et al, eds., Lippincott Williams & Wilkins, 2005.

Sustained-release preparations may be used for delivery of active agents. Suitable examples of sustained-release preparations include semi-permeable matrices of solid hydrophobic polymers containing the antibody, which matrices are in the form of shaped articles, e.g. films, suppositories or microcapsules. Examples of sustained-release matrices include polyesters, hydrogels (for example, poly(2-hydroxyethyl-methacrylate), or poly (vinylalcohol)), polylactides (U.S. Pat. No. 3,773,919), copolymers of L-glutamic acid and ethyl-L glutamate, non-degradable ethylene-vinyl acetate, degradable lactic acid-glycolic acid copolymers, and poly-D-(–)-3-hydroxybutyric acid.

As described above nucleic acids may also be used in methods of treatment. Nucleic acid for use in the invention may be delivered to cells of interest using any suitable technique known in the art. Nucleic acid (optionally contained in a vector) may be delivered to a patient's cells using in vivo or ex vivo techniques. For in vivo techniques, transfection with viral vectors (such as adenovirus, Herpes simplex I virus, or adeno-associated virus) and lipid-based systems (useful lipids for lipid-mediated transfer of the gene are DOTMA, DOPE and DC-Chol, for example) may be used (see, for example, Anderson et al., Science 256: 808-813 (1992). See also WO 93/25673).

In ex vivo techniques, the nucleic acid is introduced into isolated cells of the patient with the modified cells being administered to the patient either directly or, for example, encapsulated within porous membranes which are implanted into the patient (see, e.g. U.S. Pat. Nos. 4,892,538 and 5,283,187). Techniques available for introducing nucleic acids into viable cells may include the use of retroviral vectors, liposomes, electroporation, microinjection, cell fusion, DEAE-dextran, the calcium phosphate precipitation method, etc.

The active agents may be administered in a localised manner to a tumour site or other desired site or may be delivered in a manner in which it targets tumour or other cells. Targeting therapies may be used to deliver the active agents more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Administration

In embodiments of the invention, where an antibody molecule of the invention is used in combination with a second agent, e.g. a chemotherapeutic agent, the antibody may be administered simultaneously, separately or sequentially with the second agent. Where administered separately or sequentially, they may be administered within any suitable time period e.g. within 1, 2, 3, 6, 12, 24, 48 or 72 hours of each other. In preferred embodiments, they are administered within 6, preferably within 2, more preferably within 1, most preferably within 20 minutes of each other.

Dose

The antibody molecules or nucleic acid molecules encoding said antibody molecules and, optionally, chemotherapeutic agents of and for use in the invention are suitably administered to an individual in a "therapeutically effective amount", this being sufficient to show benefit to the individual. The actual dosage regimen will depend on a number of factors including the condition being treated, its severity, the patient being treated, the agents being used, and will be at the discretion of the physician.

In one embodiment of the methods, methods in which combinations of two or more active agents are used, the agents are administered in doses which produce a potentiating ratio.

The term "potentiating ratio" in the context of the present invention is used to indicate that two components, e.g. antibody molecule, chemotherapeutic agents etc. are present in a ratio such that the cytotoxic activity of the combination is greater than that of either component alone or of the additive activity that would be predicted for the combinations based on the activities of the individual components.

Thus in a potentiating ratio, the individual components act synergistically.

Synergism may be defined using a number of methods.

In one method, synergism may be determined by calculating the combination index (CI) according to the method of Chou and Talalay. CI values of 1, <1, and >1 indicate additive, synergistic and antagonistic effects respectively.

In one embodiment of the invention, the EGF antibody and the chemotherapeutic agent are present in concentrations sufficient to produce a CI of less than 1, such as less than 0.85. Likewise, in another embodiment of the invention, the first EGF antibody and the second EGF inhibitor are present in concentrations sufficient to produce a CI of less than 1, such as less than 0.85.

Synergism is preferably defined as an RI of greater than unity using the method of Kern as modified by Romaneli (1998a, b). The RI may be calculated as the ratio of expected cell survival (Sep, defined as the product of the survival observed with component A alone and the survival observed with component B alone) to the observed cell survival (Sobs) for the combination of A and B(RI=Se/Sobs). Synergism may then be defined as an RI of greater than unity.

In one embodiment of the invention, the EGF antibody and the chemotherapeutic agent are provided in concentrations sufficient to produce an RI of greater than 1.5, such as greater than 2.0, for example greater than 2.25.

Thus in one embodiment the combined medicament produces a synergistic effect when used to treat tumour cells.

In one embodiment of the invention, in which a bispecific antibody is used, the bispecific antibody may be provided in sufficient concentration to provide an effect which is supraadditive/synergistic over the expected effect of two separate antibodies each specific for a different one of the EGFs for which the bispecific antibody has binding specificity. In such embodiments, synergism may be assessed using the methods defined above, modified such that the bispecific antibody is considered to be the combination i.e. A+B and the individual (i.e. non-bispecific) antibodies are considered to be individual components, e.g. component A and component B.

The optimal dose can be determined by physicians based on a number of parameters including, for example, age, sex, weight, severity of the condition being treated, the active ingredient being administered and the route of administration.

The invention will now be described further in the following non-limiting examples with reference made to the accompanying drawings in which:

FIG. 1 illustrates synergistic attenuation of MDA-MB231 cell proliferation following AREG/HB-EGF silencing by siRNA. Cells were transfected with AREG siRNA (10 nM), HB-EGF siRNA (10 nM) or a mock control. Cell proliferation was analysed by MTT assay 48 hr after transfection/chemotherapy;

FIG. 2 illustrates HCT116 cell proliferation following HB-EGF silencing by siRNA and/or treatment with AREG antibody. Cells were transfected with HB-EGF siRNA (50 nM) or a control siRNA (50 nM). Cell proliferation was analysed by MTT assay 72 hr after transfection;

FIG. 3 illustrates RI values calculated by MTT cell viability assays in response to HBEGF siRNA and AREG antibodies. The RI value is calculated as the ratio of expected survival (Sexp defined as the product of the survival observed with drug A alone and the survival observed with drug B alone) to the observed cell survival (Sobs) for the combination of A and B. (RI=Sexp/Sobs). Synergism is defined as RI>1;

FIG. 4 illustrates alignment of EGF-like family members. HBEGF (Sequence ID No. 11), AREG (Sequence ID No. 12), EREG (Sequence ID No. 13), BTC (Sequence ID No. 14) and TGF-α (Sequence ID No. 15) have been aligned. A consensus sequence (Sequence ID No. 16) is also shown. Yellow residues show homology between all five members. Blue shows homology between more than 2 of the family members FIG. 5 illustrates alignment of AREG (Sequence ID No. 12) and HBEGF (Sequence ID No. 11) protein sequences. A consensus sequence (Sequence ID No. 17) is also shown. The alignments show homologous regions of the two proteins (highlighted in grey). The region produced for the antigen is shown underlined in the figure.

FIG. 6 illustrates cloning of AREG/HBEGF fragment a) Amplification of HBEGF/AREG fragment from cDNA library. The fragment was amplified from heart cDNA and PCR reaction was analysed on 1.5% agarose gel stained with ethidium bromide. b) PCR amplification was carried out colonies to identify colonies that had the AREG/HBEGF fragment successful cloned into the expression vector. PCR reaction was analysed on 1.5% agarose gel stained with ethidium bromide. Any positive colonies were selected for sequence and expression analysis FIG. 7 illustrates a) the Elution profile of the purification of antigen from 500 ml culture volume. Pellet from culture was resuspended in 8M Urea and then purified by mature of the 6× Histidine tag. The elution samples were collected and analysed by SDS-PAGE (figure B). The gel was stained with coomassie blue;

FIG. 8 illustrates different AREG fragments for screening of bispecific clones;

FIG. 9 illustrates ELISA screening of HBEGF/AREG monoclonal antibodies against recombinant protein made in house for AREG and HBEGF and R and D systems recombinant protein for human AREG and HBEGF. Monoclonal antibodies were also screened against a negative control protein produced by similar method; (from left to right for each antibody, HBEGF, AREGfgt5, Negative, Rec hum HB-EGF and Rec hum AREG);

Figure 12:
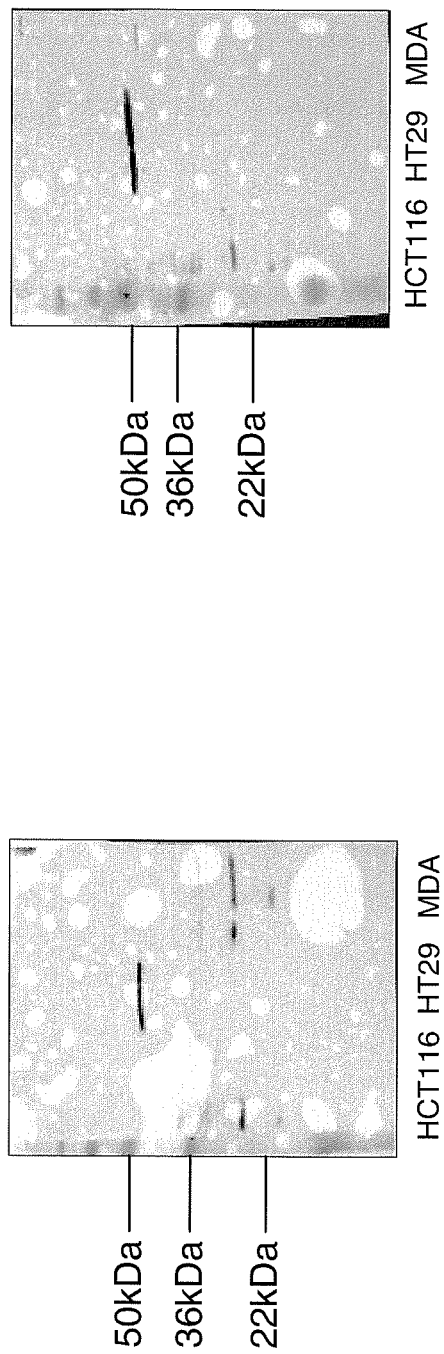
Figure 13:
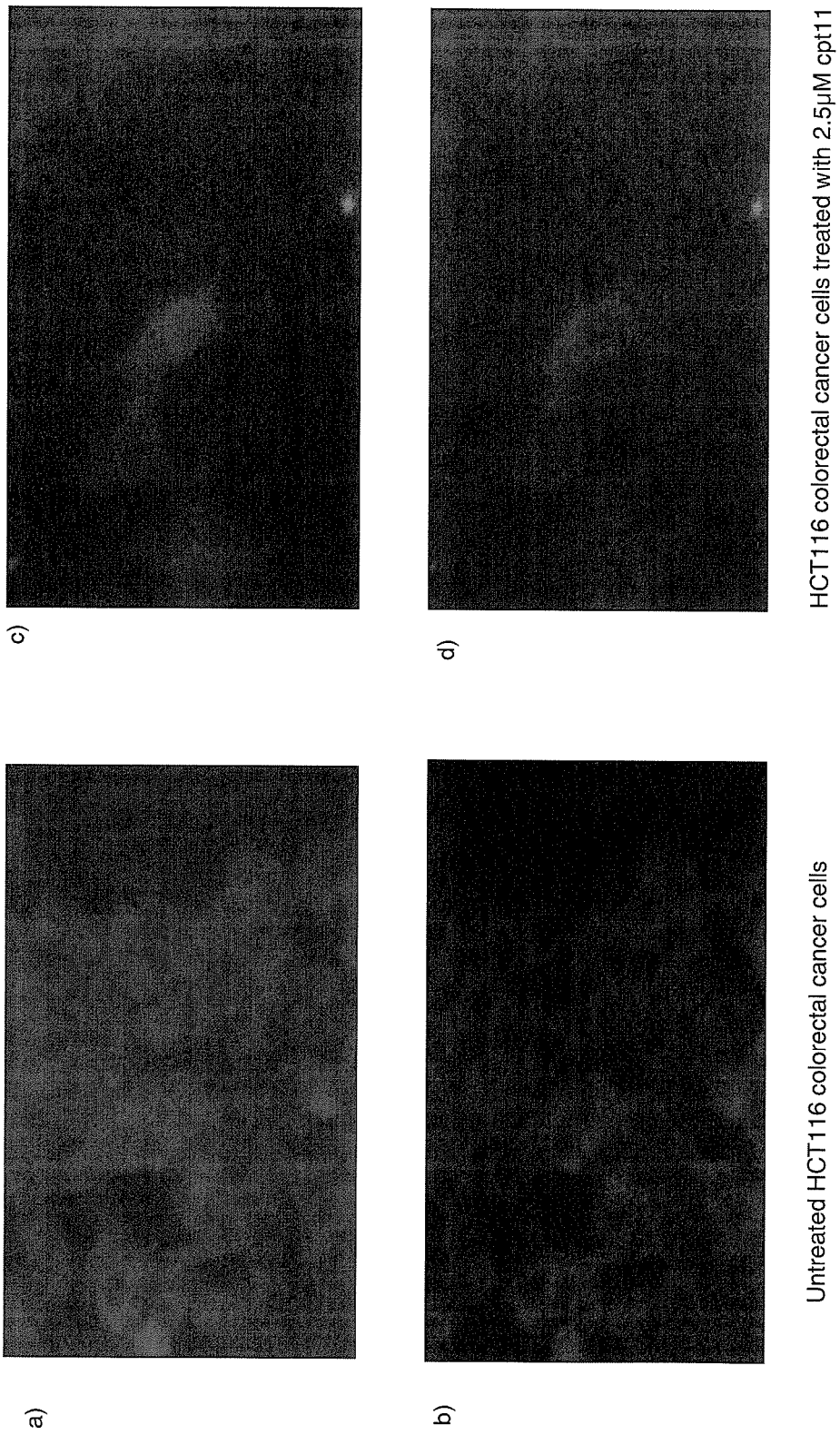

FIG. 12 illustrators Western blot analysis of AREG/HBEGF monoclonal antibodies against whole cell lysates from colorectal cell lines HCT116 and HT29 and breast cancer cell line MDA-MB231. Whole cell lysates from HCT116 and HT29 cell lines were prepared and ran on SDS-PAGE. Blots were probed with AREG/HBEGF monoclonal antibodies;

FIG. 13 illustrates the results of immunofluorscent staining using AREG/HBEGF monoclonal antibody 8D7 with FITC labelled AREG/HBEGF demonstrating positive staining in both CPT11 untreated (a and b) and (c and d) treated HCT116

Figure 14A:
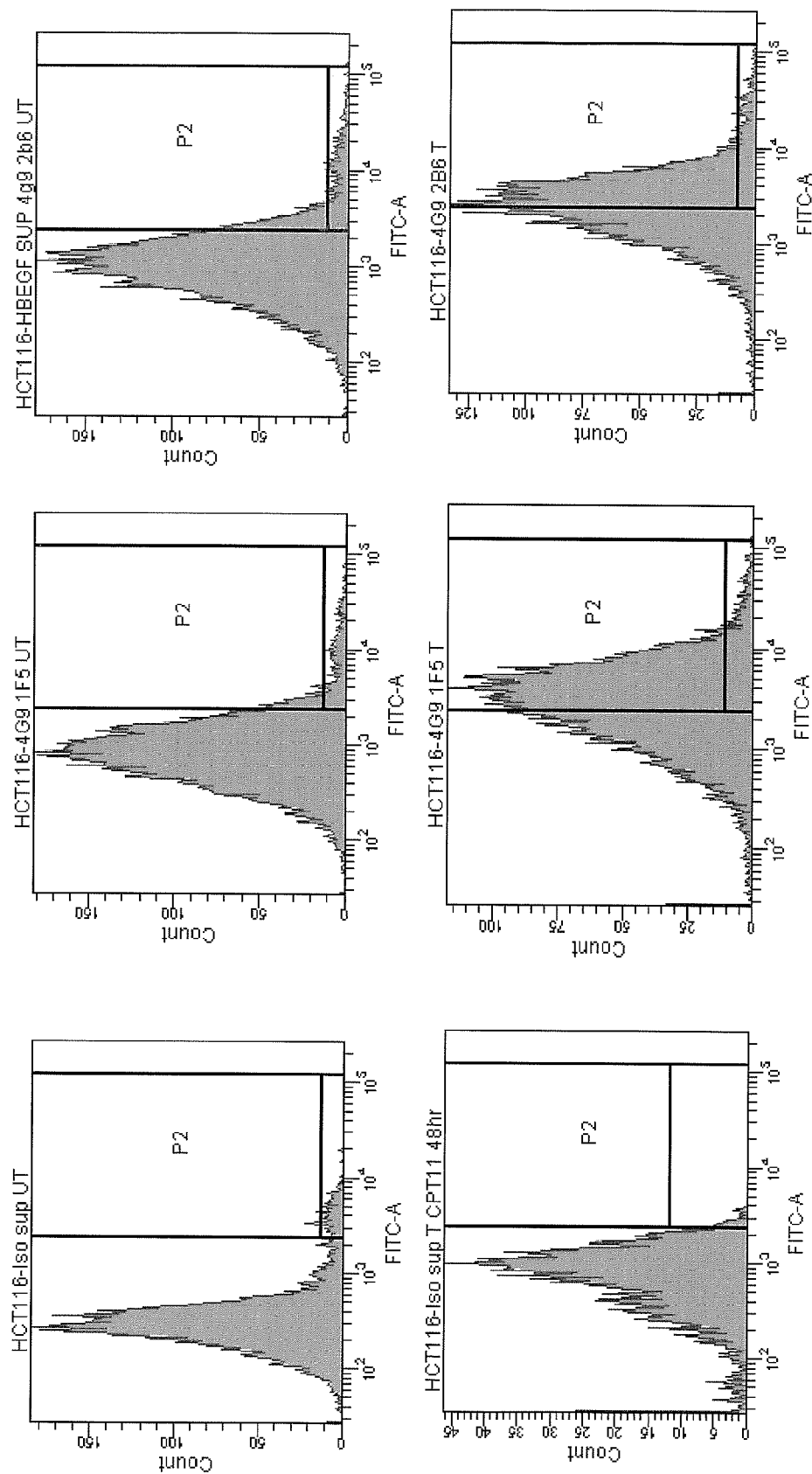
Figure 14B:
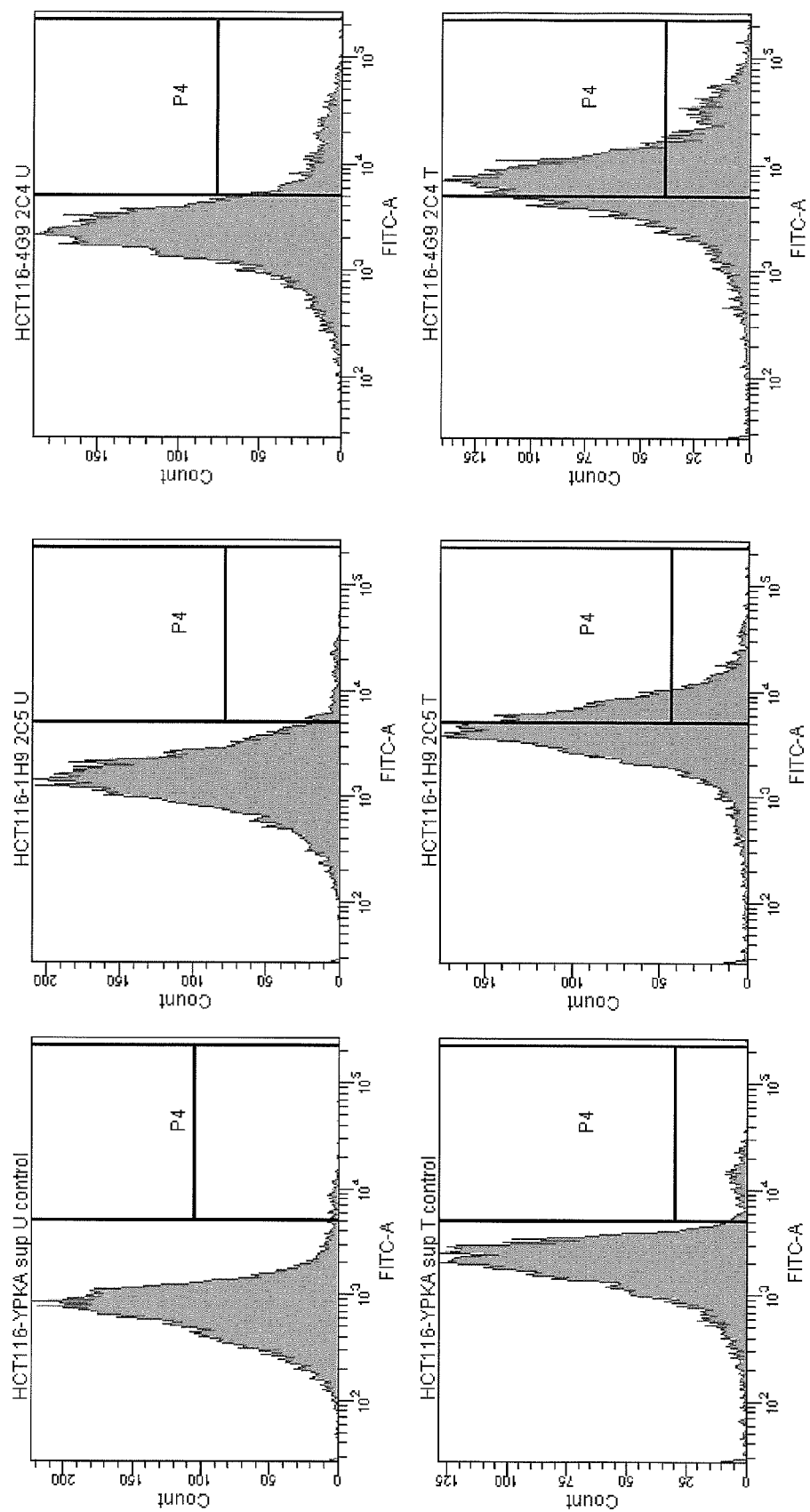

FIG. 14a illustrates FACS analysis of HCT116 colorectal cancer cell line treated with or without 2.5 µM irinotecan for 48 hours. Following treatment cells were stained with HBEGF/AREG monoclonal antibodies and analysed by FACS;

FIG. 14b illustrates FACS analysis of HCT116 colorectal cancer cell line treated with or without 2.5 µM irinotecan for 48 hours. Following treatment cells were stained with HBEGF/AREG monoclonal antibodies and analysed by FACS.

Figure 15:
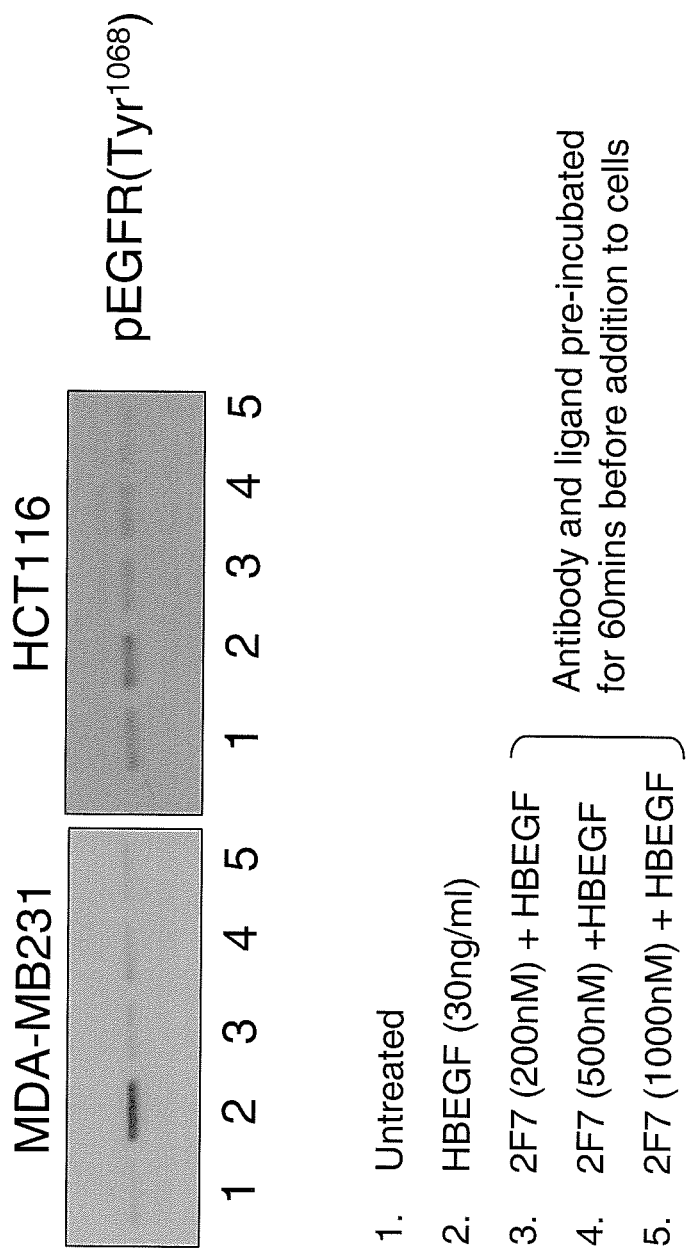

FIG. 15 illustrates inhibition of ligand stimulation phosphorylation of EGFR in MDA-MB231 cells and HCT116 cells. Cells were serum starved before addition of antibody and ligand. Cross-specific antibody (8d7 1f6 2f7, i.e. "2F7") was pre-incubated with recombinant HBEGF for 1 hour before addition to cells. Cells were stimulated for 20 mins before preparation of cell lysates. 30 µg of protein was loaded on SDS-PAGE gel and transferred to nitrocellulose membrane. The membrane was probed with anti pEGFR(Tyr$^{1068}$)

Figure 16:
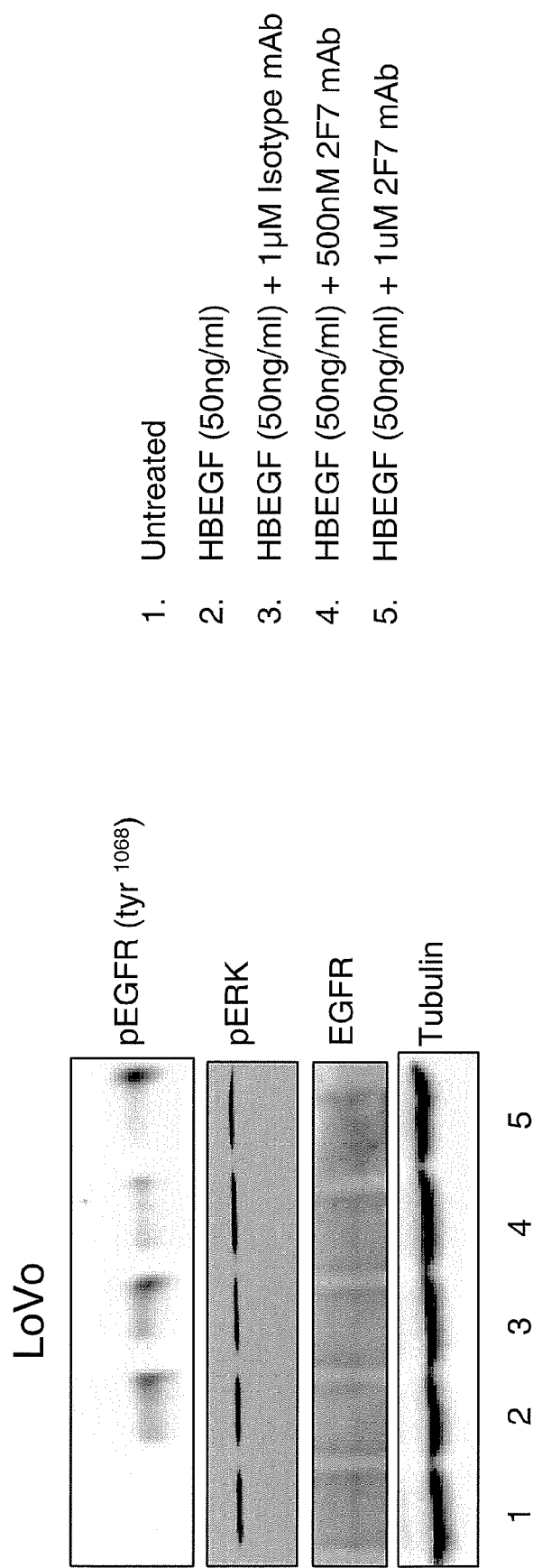

FIG. 16 illustrates inhibition of ligand stimulation phosphorylation of EGFR in LoVo cells. Cells were serum starved before addition of antibody and ligand. Cross-specific antibody (8d7 1f6 2f7, i.e. "2F7") was pre-incubated with recombinant HBEGF for 1 hour before addition to cells. Cells were stimulated for 20 mins before preparation of cell lysates. 30 µg of protein was loaded on SDS-PAGE gel and transferred to nitrocellulose membrane. The membrane was probed with anti pEGFR(Tyr 1068)

Figure 17:
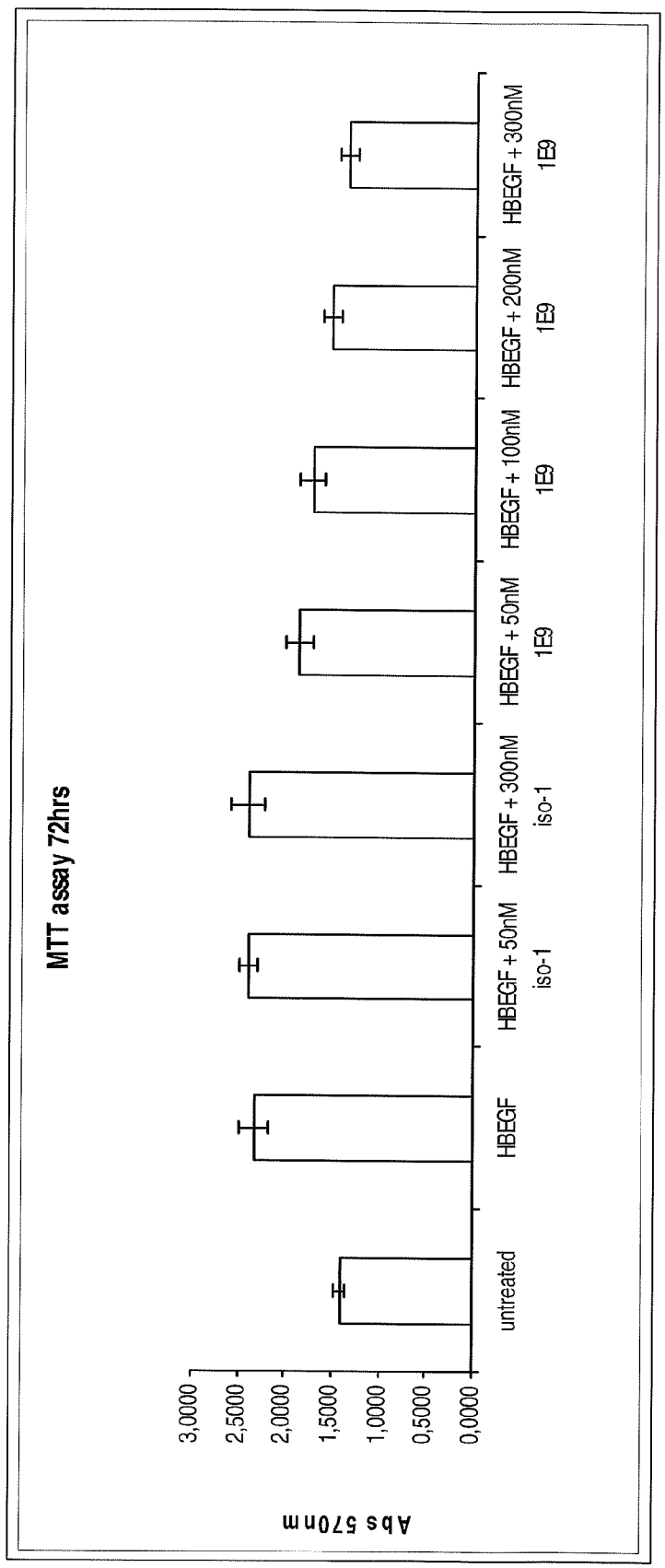

FIG. 17 shows a graph representing cell proliferation following treatment with recombinant HBEGF and cross-specific antibody (8d7 1c8 1e9 i.e. "1E9"). Different concentrations of cross-specific antibody was preincubated with ligand for an hour before addition to cells. Cell viability was assessed 48 hrs after treatment by MTT assay.

Figure 18:
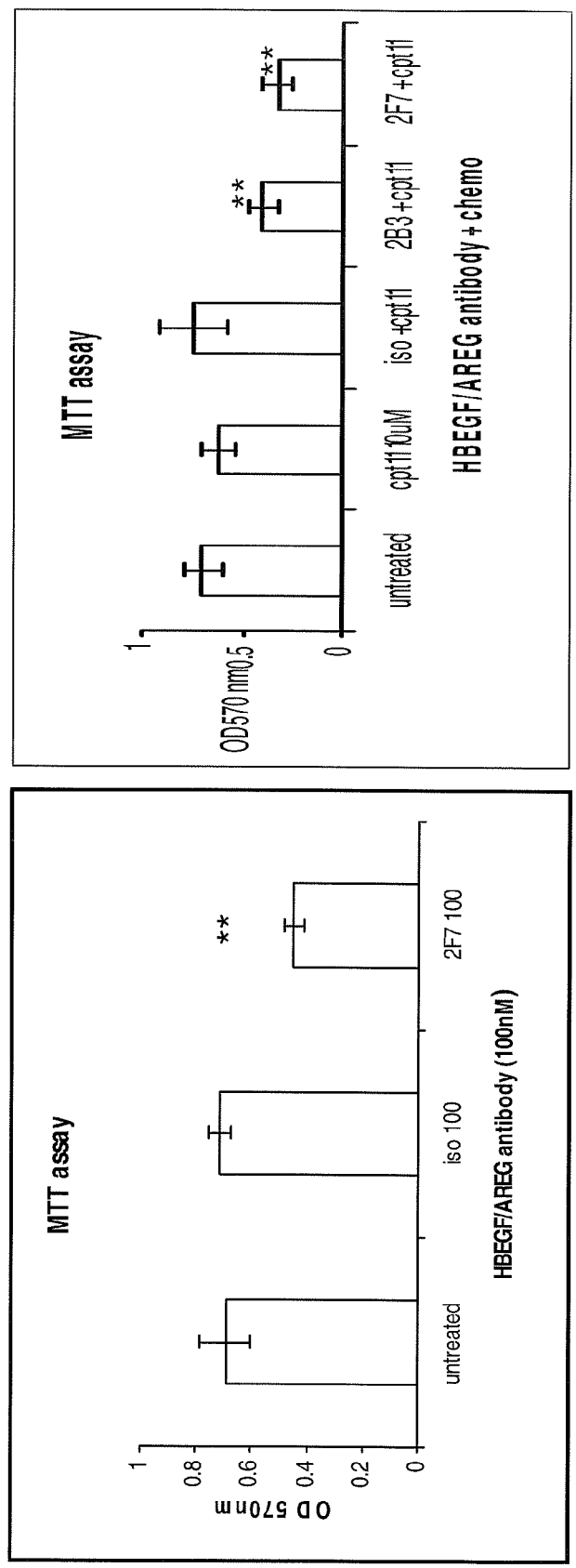

FIG. 18 shows bar charts which illustrate cancer cell proliferation following treatment with HBEGF/AREG cross-specific antibodies in combination with chemotherapy. Cells were treated with 100 nM isotype control or 100 nM cross-specific antibody (8d7 1f6 2f7 i.e. "2F7" or 8d7 1f6 2b3 i.e. "2B3" alone or in combination with 10 µM cpt11. Cells were analysed by MTT assay after 72 hrs treatment. ** indicates statistically significant P<0.001. 2B3 RI value is 0.99 therefore an additive effect. 2F7 RI value is 1.1 therefore (slightly) synergistic.

Figure 19:
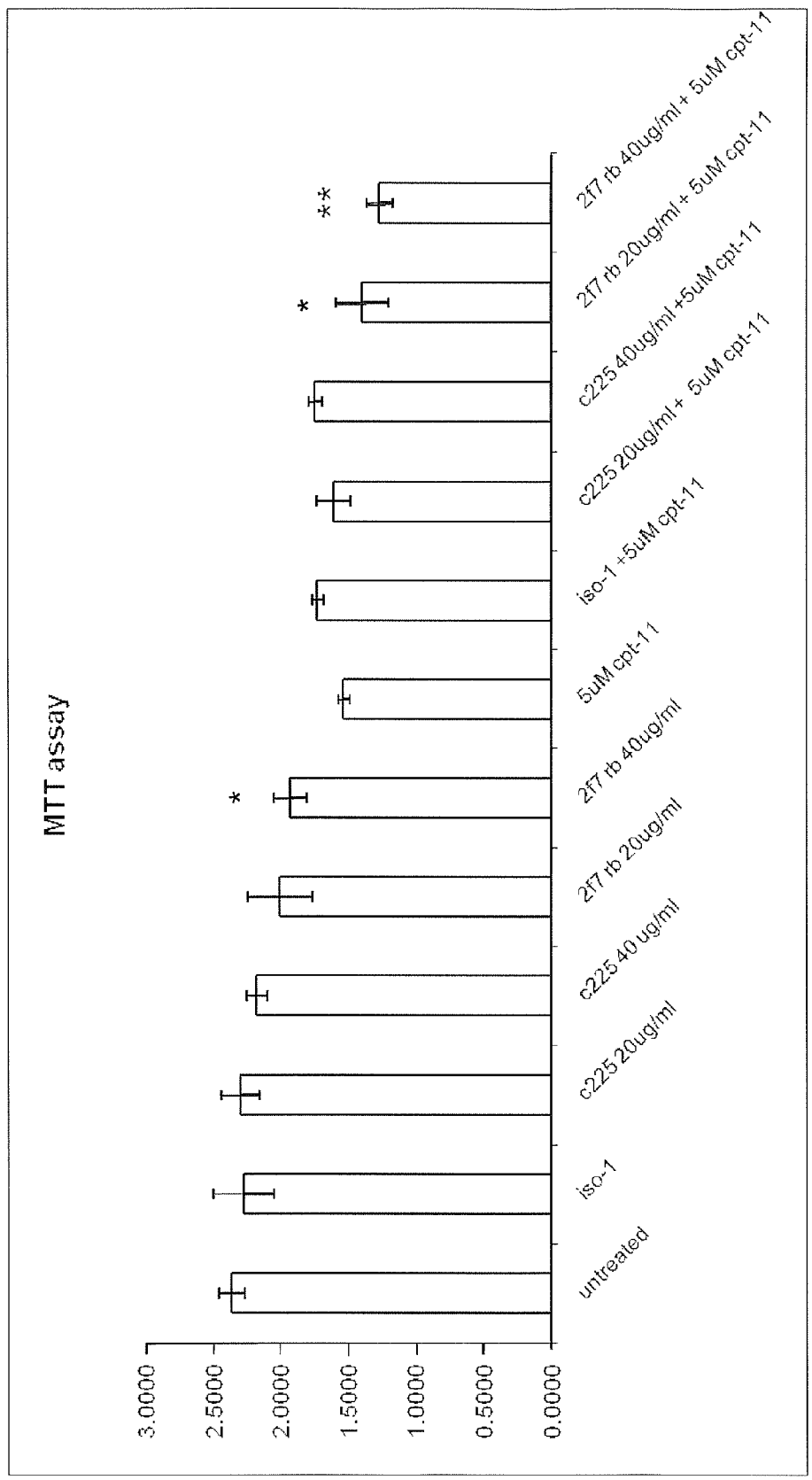

FIG. 19 shows a bar chart which illustrates a comparison of cross-specific antibody (8d7 1f6 2f7 i.e. "2F7") to commercial Cetuximab "c225". Antibodies were added to cells at concentration of 20 ug/ml and 40 ug/ml alone and in combination with chemotherapy treatment. Cell viability was assessed 72 hrs after treatment by MTT assay. ** indicates nt P<0.001. * indicates p<0.05.

FIG. 20 illustrates the results of an invasion assay on MDA-231 breast carcinoma cell line. The invasiveness of MDA-231 cells through matrigel in the presence of 500 nM cross-specific monoclonal antibody (8d7 1c8 1e9 i.e. "1E9", 8d7 1f6 2f7 i.e. "2F7" or 8d7 1f6 2b3 i.e. "2B3" and negative control (iso-1) antibodies was assessed. The cells were left for 24 hours before being stained by Hoescht and number of invaded cells per field of view counted. Panel a is a barchart summarising the results with each antibody with Panel b showing representative images obtained using negative control antibodies and 2B3 antibodies ** indicates P<0.001. * indicates p<0.05.

Figure 21:
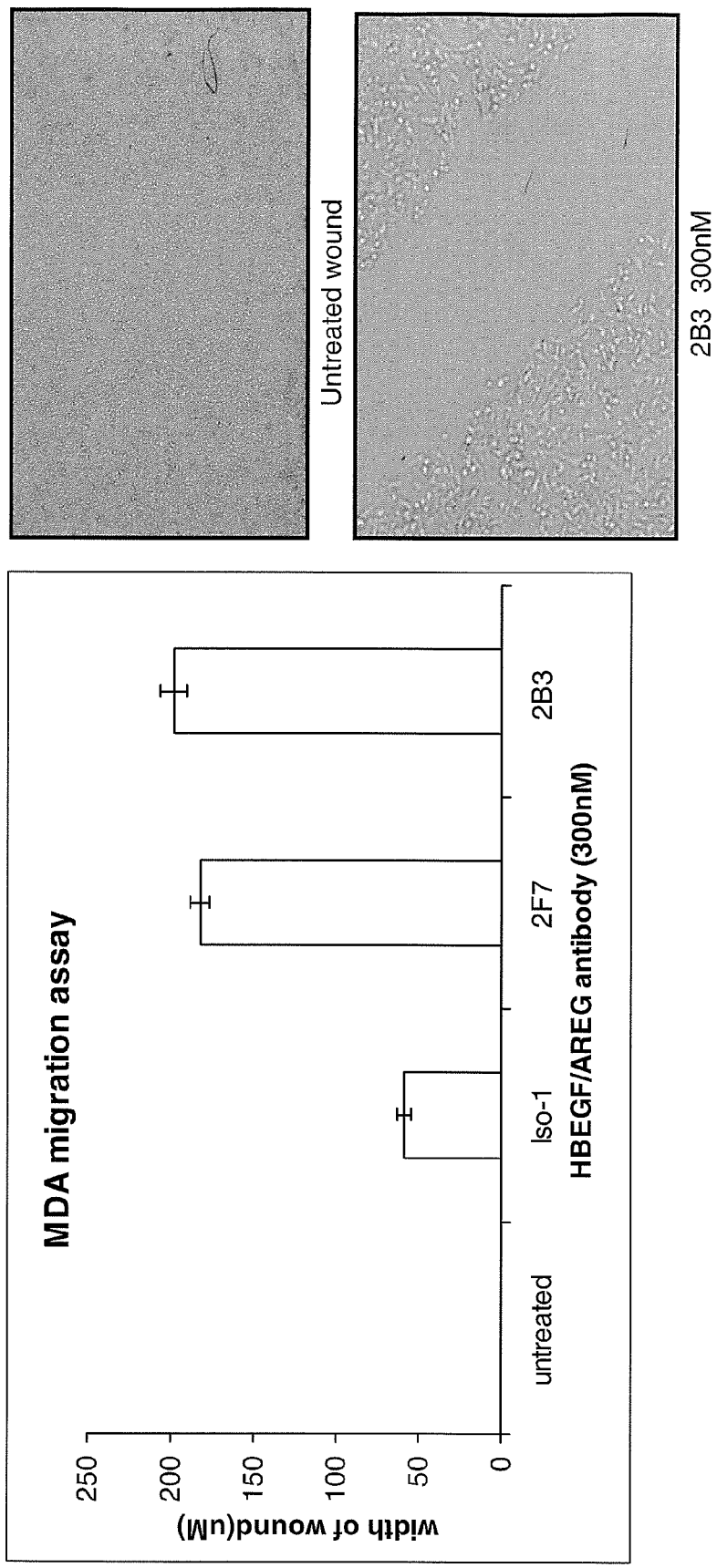

FIG. 21 illustrates the results of a migration assay on MDA-231 breast carcinoma cell line. assessed in the presence of 300 nM cross-specific monoclonal antibodies (8d7 1f6 2f7 i.e. "2F7" or 8d7 1c8 1e9 i.e. "1E9") or isotype control. The assay was left for 17 hrs before wound width was measured. The right hand panels showing representative images obtained in the absence of treatment and in the presence of 8d7 1f6 2b3 i.e. "2B3"

Figure 22:
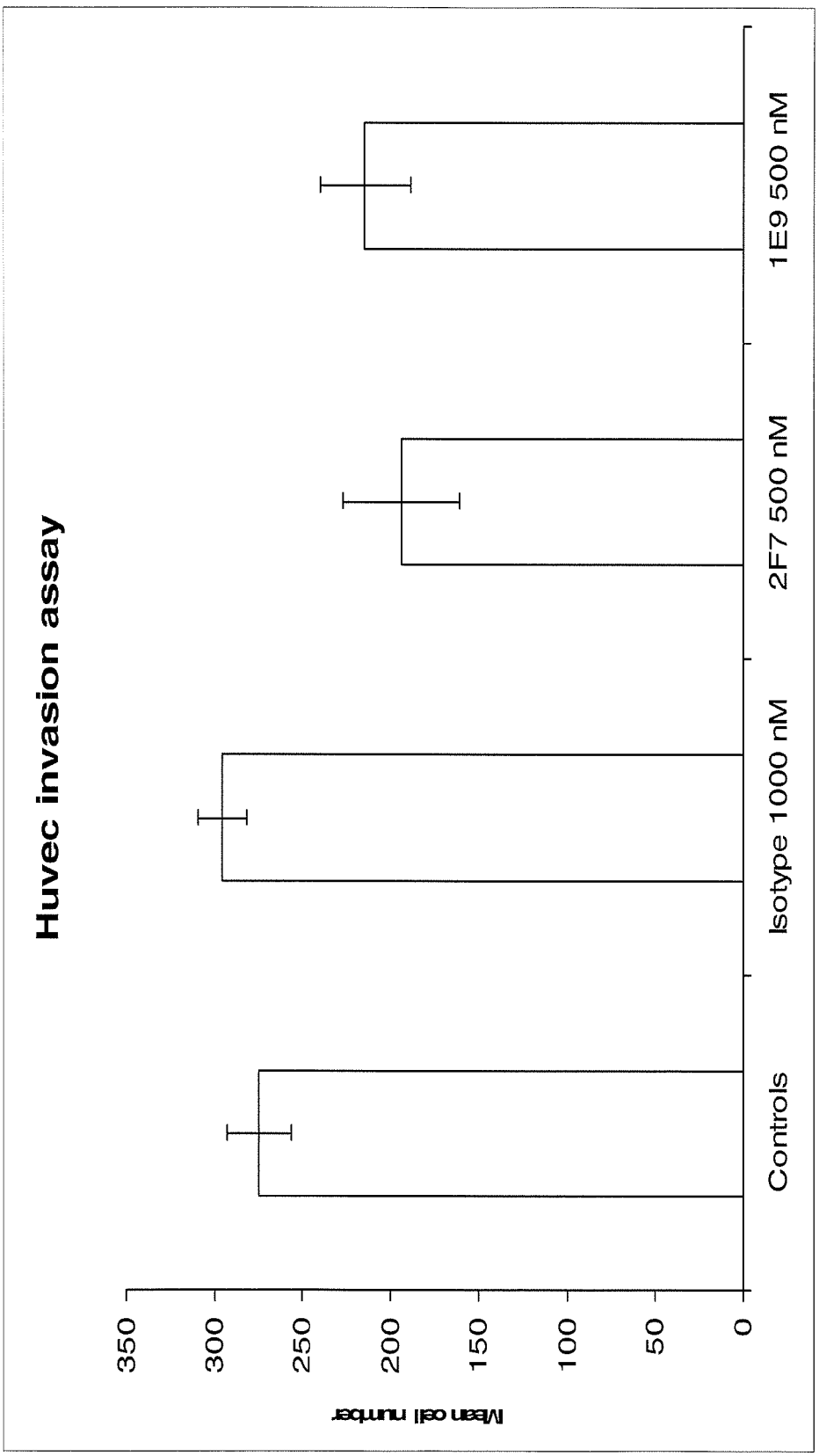

FIG. 22 illustrates the results of an invasion assay of HUVEC cells through matrigel in the presence of 500 nM Bi-specific monoclonal antibody ((8d7 1f6 2f7 i.e. "2F7" or 8d7 1c8 1e9 i.e. "1E9" and negative control antibodies. The cells were left for 24 hours before being stained by Hoescht and number of invaded cells per field of view counted.

Figure 23:
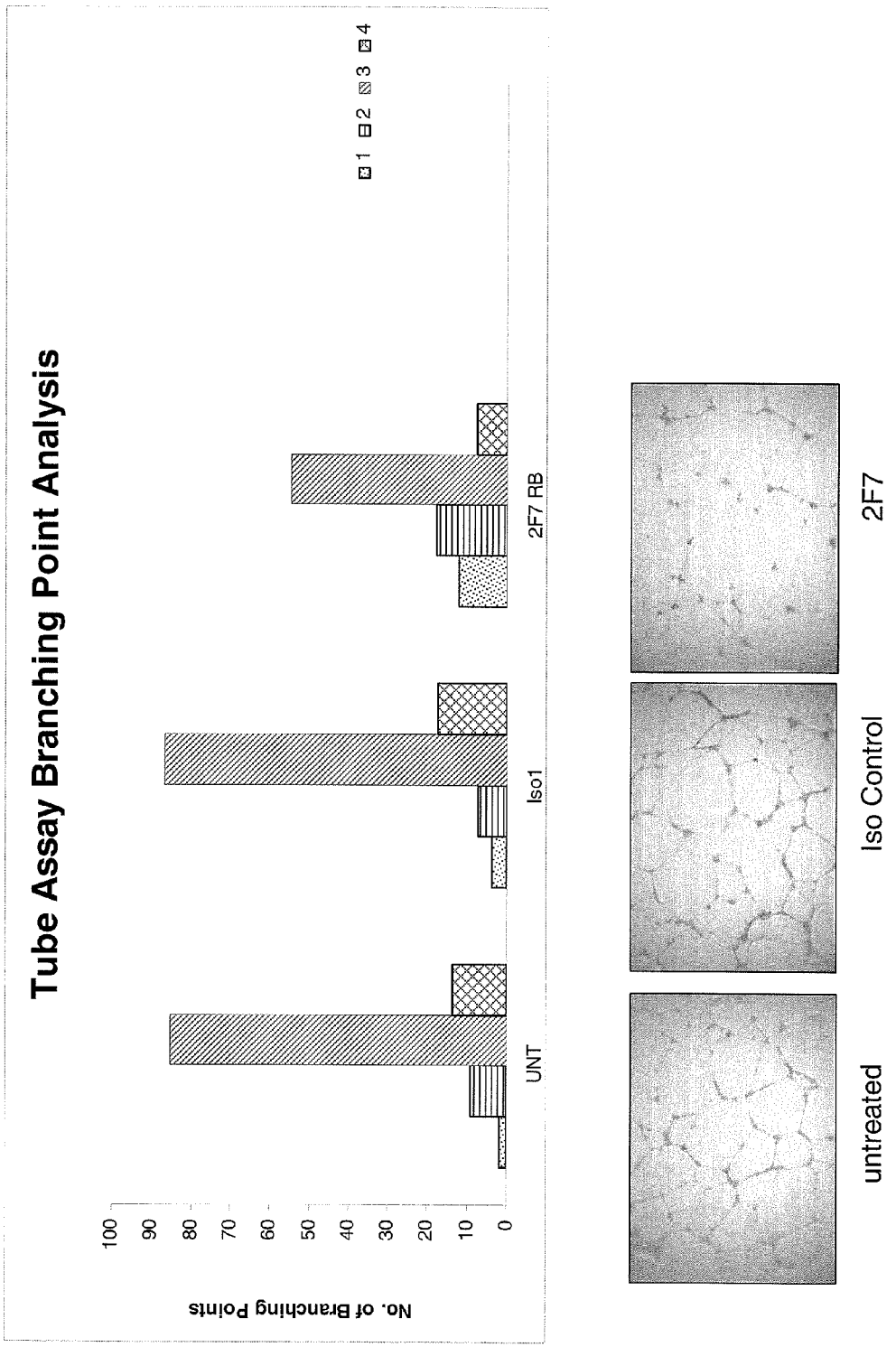

FIG. 23 illustrates tube assay analysis of cross-specific antibody. Huvec cells were seeded in the presence of cross-specific antibodies or control antibodies in wells coated with matrigel. Tube structure was analysed after 17 hrs. Images were taken and branching points around nodes counted. The lower panels show representative images with the upper panel illustrating in barchart format the number of branching points around nodes for untreated cells, cells treated with a control antibody and cells treated with the 8d7 1f6 2f7 antibodies.

Figure 24:
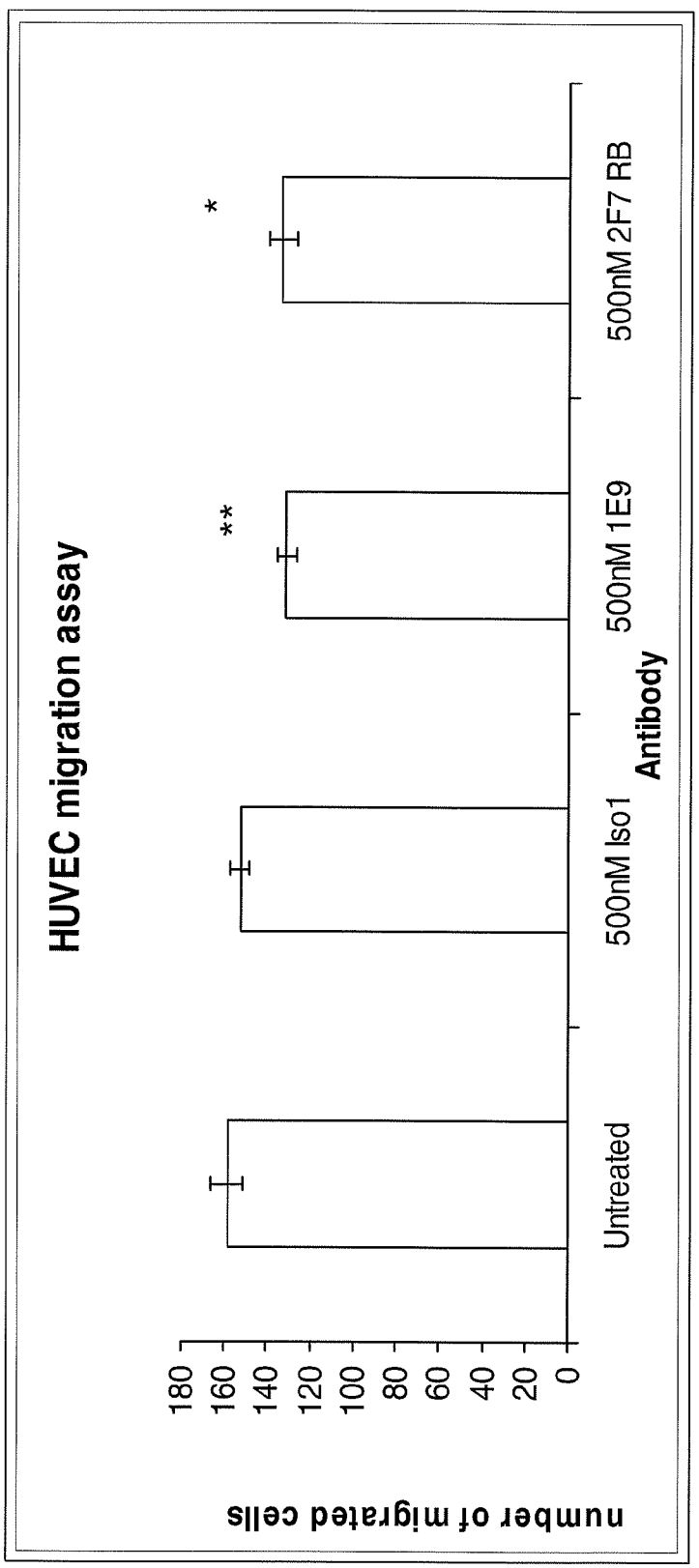

FIG. 24 illustrates the results of a migration assay of HUVEC cells in the presence of 500 nM cross-specific monoclonal antibody and negative control antibodies using a Boyden chamber assay. The cells were left for 24 hours before being stained by Hoescht and number of invaded cells per field of view counted. * p<0.05, ** p<0.001

8d7 1c8 1e9 antibody, 8d7 1f6 2f7 antibody and 8d7 1f6 2b3

EXAMPLES

Methods

Cell Lines and Culture Conditions

The MDA-MB231 human breast carcinoma cell line and the HT29 human colorectal carcinoma cell line were maintained in in Dulbecco's Modified Eagle's Medium (DMEM, Invitrogen, UK). The HCT116 (p53 wild type) human colorectal adenocarcinoma cell line was maintained in McCoys (Invitrogen, UK). All medium was supplemented with 10% FCS normal (Invitrogen, UK) or dialysed (Autogene Bioclear, UK)), 1% pen/strep, 1% L-Glutamine (All Invitrogen, UK).

RNA Interference

AREG, HB-EGF and Control siRNAs and Dharmafect 4 transfection reagent were obtained from Dharmacon, (Lafayette, Colo., USA).

Cells were seeded at 5 000 cells per well in a 96 well plate or 5×10$^5$ cells per well in a 6 well plate. The cells were cultured for 24 hours before transfection. The siRNA was made up to 100 nM in serum free DMEM and left for 5 minutes at room temperature. The Dharmafect transfection reagent was also made up in the serum free DMEM and incubated for 5 minutes at room temperature. The transfection reagent was added to the siRNA and incubated at room temperature for 20 minutes. The media was removed from the plate wells and antibiotic free DMEM was added to the wells. After 20 minutes the siRNA was added dropwise to the wells. The plates were incubated at 37° C. for 48 hours.

MTT Assay

Cell viability was assessed by 3-(4,5-dimethylthiazol-2-yl)-2,5-diphenyltetrazolium bromide (MTT, Sigma) assay (Mosmann, 1983). To assess chemotherapy/siRNA interactions 5000 cells were seeded per well on 96 well plate. After 24 hours cells were transfected with siRNA and treated with various chemotherapeutic agents at different concentrations. After 48 hours MTT (1.0 mg/ml) was added to each well and cells were incubated at 37° C. for 2 hours. The culture media was removed and formazan crystals were reabsorbed in 200 μl DMSO. Cell viability was determined by reading the absorbance of each well at 570 nm using a microplate reader (Tecan Sunrise, Biorad, UK).

Cloning

The DNA sequence encoding the HBEGF protein was amplified by PCR from a cDNA library using gene-specific primers (FIG. 6b). The HBEGF gene was cloned into the bacterial expression vector pRSETa allowing the incorporation of a hexahistidine tag onto the N-terminus of the recombinant protein. This construct was then used to transform competent BL21 DE3 *E. coli* cells (Invitrogen). Positive transformants were selected by colony PCR using vector-specific primers flanking the multiple cloning site (FIG. 6b).

Expression of Recombinant HBEGF Protein

The positive clones were propagated overnight at 37° C. in 5 mls of Luria-Bertani (LB) broth supplemented with 50 μm ampicillin. A 300 μl aliquot of this culture was retained for inoculation of secondary cultures and the remainder of the sample was miniprepped using the Qiagen miniprep kit and the sequence verified by DNA sequencing.

Three secondary cultures were inoculated to allow visualisation of protein expression. The cultures were induced with IPTG (final concentration 1 mM) when the cultures had an OD of 0.2, 0.5 and 1.0 ($A_{550}$) respectively and then left for 4 hrs at 37° C. The cells were then harvested by centrifugation at 4000 rpm for 15 mins and the pellet resuspended in 1 ml of PBS/0.1% Igepal supplemented with 1 μl of lysonase. Samples were then analysed by SDS-PAGE and western blotting to confirm expression of the protein. The SDS-PAGE gel was stained overnight in coomassie blue and destained the following day.

The recombinant HBEGF protein was then expressed in 500 mls of LB broth supplemented with ampicillin, using the secondary culture as an inoculant and induced with IPTG once the culture had reached the optimal optical density. The culture was centrifuged at 5000 rpm for 15 mins and the pellet retained for protein purification.

Protein Purification

The induced recombinant protein was solubilised in 50 mls of 8 M urea buffer (480 g Urea, 29 g NaCl, 3.12 g NaH2PO4 (dihydrate), 0.34 g Imidazole) overnight. The solution was centrifuged at 6000 rpm for 1 hr, after which the supernatant was filtered using 0.8 μm gyrodisc filters before purification.

The protein was purified by its N-terminal hexahistidine tag and refolded using on-column refolding by immobilized metal affinity chromatography. Chelating hi-trap columns (Amersham Biosciences) were charged using 100 mM nickel sulphate before attachment to the Aktaprime. Refolding takes place by the exchange of the 8 M urea buffer with a 5 mM imidazole wash buffer (29 g NaCl, 3.12 g NaH2PO4 (dihydrate) 0.34 g Imidazole, pH 8.0) and elution of the protein using a 500 mM imidazole elution buffer (29 g NaCl, 3.12 g NaH2PO4 (dihydrate), 34 g Imidazole). The elution profile of the purified recombinant protein was recorded and can be seen in FIG. 7a.

Figure 7B:
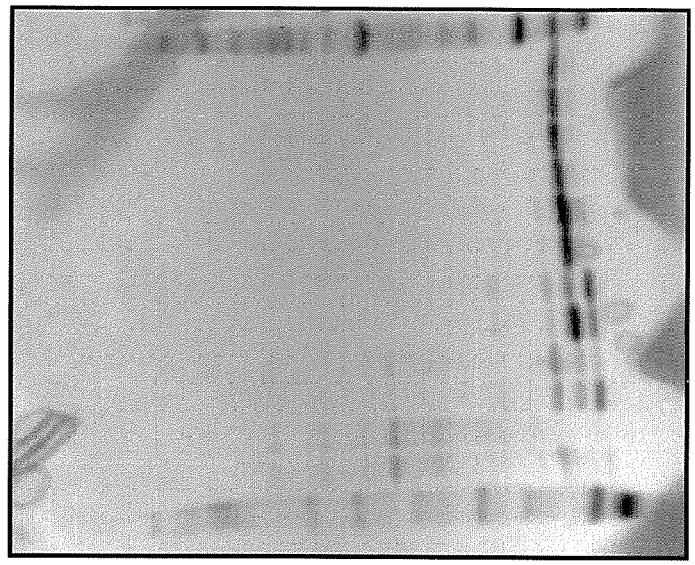
Figure 7A:
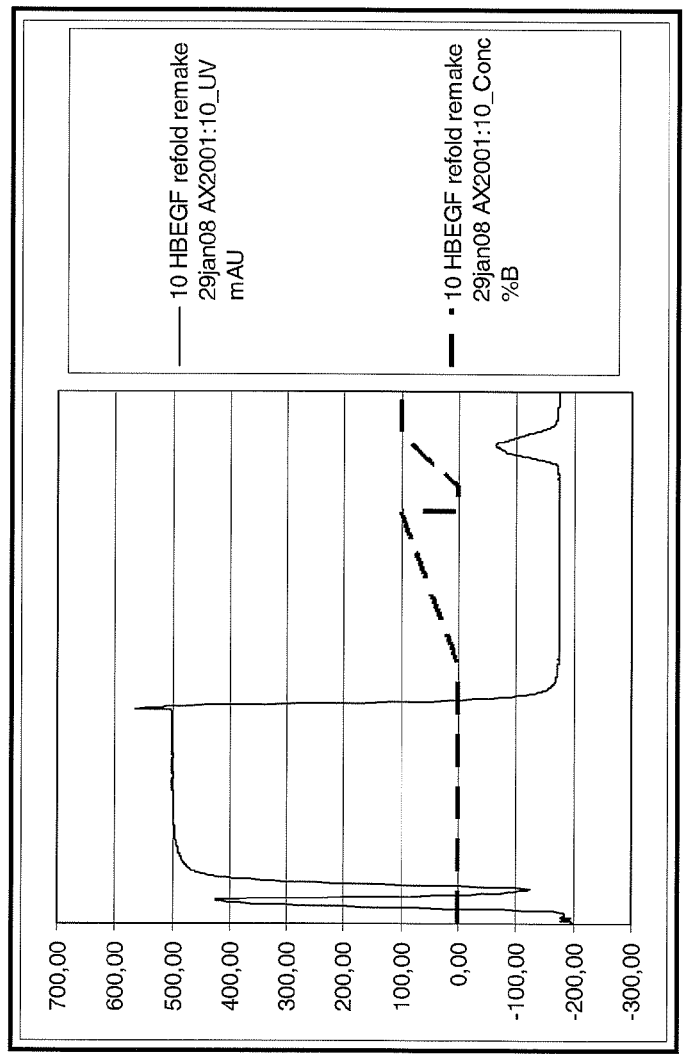
Figure 8:
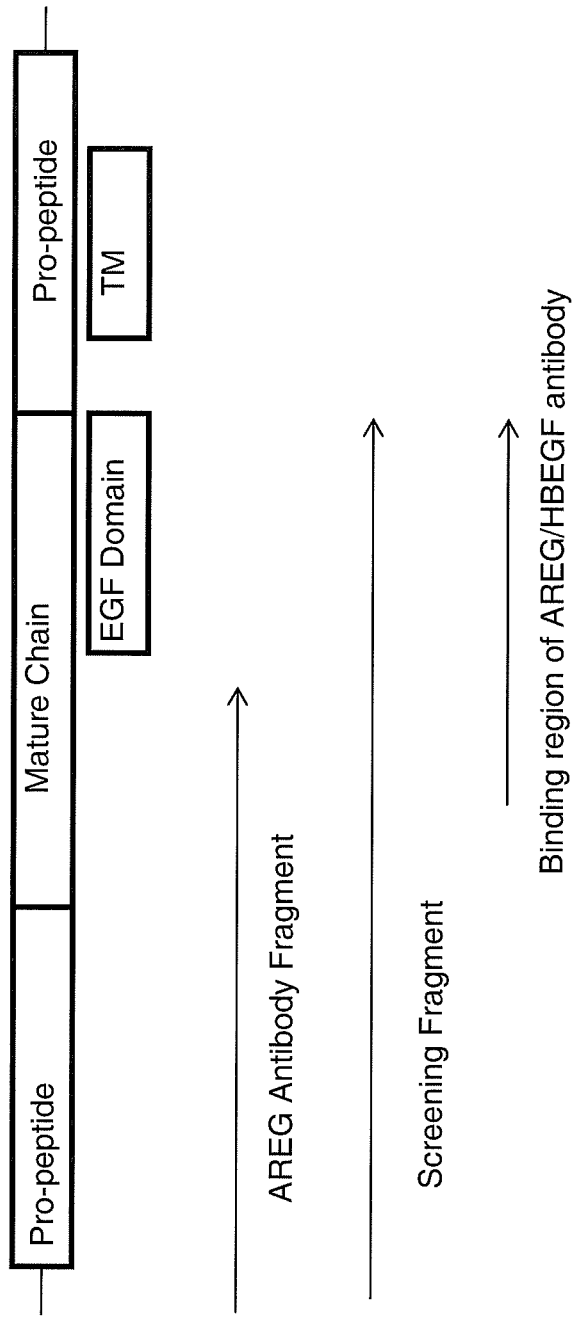

The eluted fractions were subjected to SDS-PAGE analysis to confirm recombinant protein presence in eluted fractions. The gels were stained with coomassie blue overnight and subsequently destained to determine the fractions containing the HBEGF protein (FIG. 7b).

Antibody Generation

The refolded protein was used as an immunogen to generate monoclonal antibodies. Five BALE/C mice were immunized at three weekly intervals with 150 μg of purified recombinant protein and the antibody titre was analysed after boosts three and five. A test bleed was taken from each animal and tested at 1:1000 dilutions in western blotting against 100 ng of antigen. Blots were developed using 3,3'-diaminobenzidine (DAB).

After the fifth boost, the spleen was removed from the mouse and the antibody producing B cells were fused with SP2 myeloma cells following standard protocols. Eleven days after the hybridoma fusion, the plates were examined for cell growth. Clones were screened by ELISA against recombinant protein and selected positive hybridomas were cloned twice by limiting dilution.

ELISA

The monoclonal antibodies were screened by ELISA to determine which clones should be expanded. Maxi Sorb 96 well plates were coated with recombinant antigen by adding 100 μl of coating buffer (Buffer A: 0.42 g sodium bicarbonate/100 μl $H_2O$, Buffer B: 0.53 g sodium carbonate/100 μl $H_2O$, pH 9.5) containing the screening antigen to each well (100 ng/well). A control antigen was also used to eliminate non-specific clones. The plates were incubated at 37° C. for 1 hr to allow the antigen to bind to the well and then blocked for 1 hr at room temperature by adding 200 μl PBS/3% BSA to each well.

The blocking solution was removed from the plates and 100 μl of hybridoma supernatant was added to a positive antigen and a control antigen well. The screening plates were incubated with supernatant for 1 hr on a rocker at room temperature. The plates were washed three times with PBS-T, after which 100 μl of goat anti-mouse HRP conjugated secondary antibody (1:3000) was added to each well and incubated for 1 hr at room temperature. The plates were washed three times with PBS-T and 100 μl of 3,3',5,5'-tetramethylbenzidine (TMB) was added to each well and incubated for 5 mins at 37° C. Positive wells were indicated by a colour development and the reaction was stopped by addition of 50 μl 1M HCL. Plates were read by a spectrophotometer at 450 nm and samples displaying a positive reading in the screening well (+) with a negative reading in the control well (−) were chosen for further work. The cells from the original wells were transferred into a 24 well plate and grown up.

Western Blotting

The supernatants from the hybridoma cell lines were analysed by western blotting to determine the ability of the monoclonal antibodies to detect both recombinant protein and endogenous native protein in a range of cancer cell lines. Aliquots of HCT116, HT29 and MDA whole cell lysates (~30 μg/ml) or recombinant protein were separated by SDS-PAGE and transferred onto Hybond-C Extra nitrocellulose membrane (Amersham Biosciences). The membrane was blocked by incubation in PBS/5% marvel for 1 hr at room temperature, after which it was rinsed briefly in PBS. The monoclonal antibodies were used at a 1:500 or 1:250 dilutions in PBS and incubated on the membrane overnight at 4° C. while gently rocking. The blot were then rinsed three times with PBS/1% marvel and 0.1% Tween-20 and then incubated with the goat anti-mouse HRP conjugated secondary antibody at a 1:3000 dilution for 1 hr at room temperature while shaking. The blots were then rinsed three times with the PBS/1% marvel and 0.1% Tween-20 solution, followed by a short rinse in PBS. The blots were incubated with ECL plus substrate (Amersham Biosciences) for 5 mins at room temperature prior to analysis on the Kodak imager.

Flow Cytometry Analysis

HCT116 cells were treated for 48 hours with or without 2.5 µM irinotecan. After 48 hours cells were washed in PBS. $5 \times 10^5$ cells were incubated with AREG antibodies or isotype control for 2 hours and washed in PBS. The cells were incubated with a FITC conjugated goat anti-mouse antibody for 1 hour and washed in PBS before analysis on BD FACS canto.

Tube Assay

A sterile 12-well plate was left in the freezer and matrigel was left on ice to thaw in fridge overnight. The 12-well plate was kept on ice whilst being coated with matrigel. The wells were hydrated using 1 ml of 1×PBS. PBS was then removed and 70 µl of matrigel added drop wise to plate. The plate was incubated at room temperature for 5-10 mins on even surface then incubate plate at 37° C. for 45 mins-1 h. Cells were trypsined and counted. $1 \times 10^5$ cells per well were used. Antibodies were made up to appropriate concentration and added to cells. The cells and antibodies were added dropwise to the wells to ensure even spread of cells. The plate was incubated overnight at 37° C. Images of wells were taken and branching analysis performed.

Invasion Assay

In-vitro invasion assays were performed using a modified Boyden chamber with 8 µm pore membranes. The upper membrane surface was coated with 150 µl Matrigel (1 mg/ml) and incubated at 37° C. for 5 hr in order for the Matrigel to form a gel. Cells were added ($2.5 \times 10^5$ cells in 250 41 of serum free media) in the presence of pre-determined concentrations of the appropriate antibody. Fresh complete media was added to the lower chambers (750 µl), supplemented with the same concentration of the antibody applied to the corresponding well above. All assays were carried out in duplicate and invasion plates were incubated at 37° C. and 5% $CO_2$ for 24 hours.

Cells remaining on the upper surface of the membrane were removed by wiping with cotton tips and cells which have invaded through were fixed in Carnoy's fixative for 15 minutes. After drying, the nuclei of the invaded cells was stained with Hoechst 33258 (50 ng/ml) in PBS for 30 minutes at room temperature. The chamber insert was washed twice in PBS, mounted in PermaFluor mounting medium and invaded cells viewed with a fluorescent microscope. Ten digital images of representative fields from each of the duplicate membranes were taken using a magnification of ×20. The results were analysed by counting the number of invaded cells per field of view and expressing counts relative to controls.

Wound Migration Assay $5 \times 10^5$ MDA-MB231 cells were seeded on coverslips in 6-well plate and left overnight to grow to 90% confluency. The media was removed from the cells and a scratch wound made in cells using a pipette tip. Cells were rinsed with PBS and media containing antibody at appropriate concentration and 5 ug/ml of mitomycin C added. Wounds were left to close for 17 hrs and then cells were fixed in 4% PFA in PBS for 20 mins. Coverslips with fixed cells were placed on microscope slides and images of wounds were taken and width of wound measured.

Boyden Chamber Migration Assay

In-vitro migration assays were performed using a modified Boyden chamber with 8 µm pore membranes. Cells were added ($2.5 \times 10^5$ cells in 250 µl of serum free media) in the presence of pre-determined concentrations of the appropriate antibody. Fresh complete media was added to the lower chambers (750 µl), supplemented with the same concentration of the antibody applied to the corresponding well above. All assays were carried out in duplicate and invasion plates were incubated at 37° C. and 5% $CO_2$ for 24 hours.

Cells remaining on the upper surface of the membrane were removed by wiping with cotton tips and cells which have invaded through were fixed in Carnoy's fixative for 15 minutes. After drying, the nuclei of the invaded cells was stained with Hoechst 33258 (50 ng/ml) in PBS for 30 minutes at room temperature. The chamber insert was washed twice in PBS, mounted in PermaFluor mounting medium and invaded cells viewed with a fluorescent microscope. Ten digital images of representative fields from each of the duplicate membranes were taken using a magnification of ×20. The results were analysed by counting the number of invaded cells per field of view and expressing counts relative to controls.

Phosphorylation Assay $1.5 \times 10^6$ cells were seeded in 10 $cm^3$ dish in media containing 10% serum. 24 hrs after seeding cells were serum starved for 4 hrs. Antibodies were preincubated for 1 hour with 30 ng/ml of recombinant HBEGF before being added to cells for 20 mins in 2% serum. Cells were washed 3 times in PBS containing phosphatase inhibitors and scraped. Cells were pelleted and lysed. Protein concentration was determined and 30 ug of protein ran on SDS-PAGE for western blot analysis. Blots were probed with pEGFR($Tyr^{1068}$) antibody.

3LL Lewis Lung Metastasis Model 6-8 week-old female C57bl/6 mice are injected intravenously, via the tail vein, with $5 \times 10^5$ 3LL cells, freshly harvested from culture in the log phase of growth and re-suspended in Hanks-buffered saline solution (HBSS). There is a minimum of 8 mice per treatment group. Animals are treated with a dose range of antibody or isotype control. The study is terminated and mice are sacrificed on Day 25. Lungs are removed and macro-analysis is performed to count the number of visible tumour nodes. Lungs will then be formalin-fixed and paraffin-embedded for histological examination. The number of tumour nodes is counted upon microscopic analysis of H&E sections and the tumour area are also measured using the Nikon Camera Software. Statistical significance of any differences observed in the number of metastatic lung nodes between treatment groups are assessed.

HCT116 Xenograft Model with Single Agent Antibody 6-8 week-old female BALB/c nu/nu mice are implanted subcutaneously with $1 \times 10^6$ HCT116 cells on the abdominal flank. Cells are freshly harvested from culture in the log phase of growth and resuspended in a 1:1 mixture of HBSS/BD Basement membrane matrigel mix prior to implantation. The mice are maintained under specific pathogen-free conditions. Tumour volumes are measured using the following formula: volume ($mm^3$)=0.5×(smallest diameter$^2$×largest diameter). When tumours reach an average volume of $100^{=3}$, mice are sorted into treatment groups. There is a minimum of 8 mice per treatment group. Animals are treated with a dose range of antibody or isotype control. Body weights and tumour volumes are measured 3 times weekly. The study will be terminated when tumours reach an average volume of 1000 $mm^3$. Upon sacrifice, tumours and all mouse organs are removed and formalin-fixed for histological examination. Increase in tumour volumes is plotted graphically and two-way ANOVA performed to measure statistical significance between treatment groups.

HCT116 Colorectal Xenograft Model with Chemotherapy Combination Regime

This model assesses the efficacy of an antibody+chemotherapy combination treatment regime. 6-8 week-old female BALB/c nu/nu mice are implanted subcutaneously with $1 \times 10^6$ HCT116 cells on the abdominal flank. Cells are freshly harvested from culture in the log phase of growth and resuspended in a 1:1 mixture of HBSS/BD Basement membrane matrigel mix prior to implantation. The mice are maintained under specific pathogen-free conditions. Tumour volumes are measured using the following formula: volume $(mm^3)=0.5\times$(smallest diameter$^2\times$largest diameter). When tumours reach an average volume of 100 mm$^3$, mice are sorted into treatment groups. There is a minimum of 8 mice per treatment group. Animals are treated with a dose range of antibody or isotype control in combination with chemotherapy. Body weights and tumour volumes are measured 3 times weekly. The study is terminated when tumours reach an average volume of 1000 mm$^3$. Upon sacrifice, tumours and all mouse organs are removed and formalin-fixated for histological examination. Increase in tumour volumes is plotted graphically and two-way ANOVA performed to measure statistical significance between treatment groups.

Syngeneic (4T1) Breast Metastasis Model

This model is used to assess the ability of the antibody to prevent metastasis from an orthotopic mammary fat pad tumour to mouse liver, lungs, bone and brain.

6-8 week old female BALE/c mice are implanted orthotopically in the mammary fat pad with $1 \times 10^5$ 4T1 cells, freshly harvested from culture in the log phase of growth and resuspended in HESS. Tumour volumes are measured using the following formula: volume $(mm^3)=0.5\times$(smallest diameter$^2\times$ largest diameter). After 7 days, tumour volume measurements are taken and animals are sorted into treatment groups. There is a minimum of 8 mice per treatment group. Animals are treated with a dose range of antibody or isotype control (with/without chemotherapy). Body weights and primary tumour volume measurements are recorded three times weekly. The study will be terminated when primary tumour volumes reach an average of 1000 mm$^3$. Upon sacrifice, primary tumours and all mouse organs are removed and formalin-fixed for histological examination. Metastatic tumour cell colonies in the liver are counted (4 fields of view per liver) and average number of colonies compared for all treatment groups. Statistical significance of any differences observed in the number of metastatic liver colonies between treatment groups is assessed.

MDA-231-Luc Breast Metastasis Model with Single Agent Antibody

This model is used to assess the ability of the drug to prevent metastasis from an orthotopic mammary fat pad tumour to the lymph nodes. (It may also be used to test the ability of the drug to prevent metastasis of tumour cells from the bloodstream to the lung, pancreas and spleen.) As the tumour cells are tagged with luciferase, tumour metastases can be tracked by luminescence using a Bioimager.

6-8 week-old female BALB/c nu/nu mice are implanted subcutaneously with $5 \times 10^6$ MDA-231-Luc cells on the abdominal flank. Cells are freshly harvested from culture in the log phase of growth and resuspended in a 1:1 mixture of HBSS/BD Basement membrane matrigel mix prior to implantation. The mice are maintained under specific pathogen-free conditions. Treatment begins on Day 14. Animals are sorted into treatment groups at this stage. There is a minimum of 8 mice per treatment group. Animals are treated with a dose range of antibody or isotype control (with/without chemotherapy). Body weights and tumour volumes are measured 3 times weekly. Tumour volumes are measured using the following formula: volume $(mm^3)=0.5\times$(smallest diameter$^2\times$largest diameter). At week 6-7 after implantation, bioimaging takes place to detect metastases of tumour cells to the lymph nodes. Prior to bioimaging (15 min), mice are injected intravenously, via the tail vein, with luciferin. Whole animal imaging takes place and selected tissues are removed for ex vivo imaging. Tissues are also formalin-fixed for histological examination. Growth of primary tumours and extent of metastases are assessed. Appropriate statistical tests are adopted to analyse all data.

Alternatively, tumour cells $(2\times10^6)$ may also be implanted intravenously via the tail vein. For this model, treatment begins on Day 14. Animals will be treated as above for 6 weeks. Bioimaging to detect metastatic signals in the lung, pancreas and spleen takes place from weeks 8-10.

Results

Attenuation of Cell Growth by Combination of AREG siRNA/Antibody and HBEGF siRNA.

Figure 1:
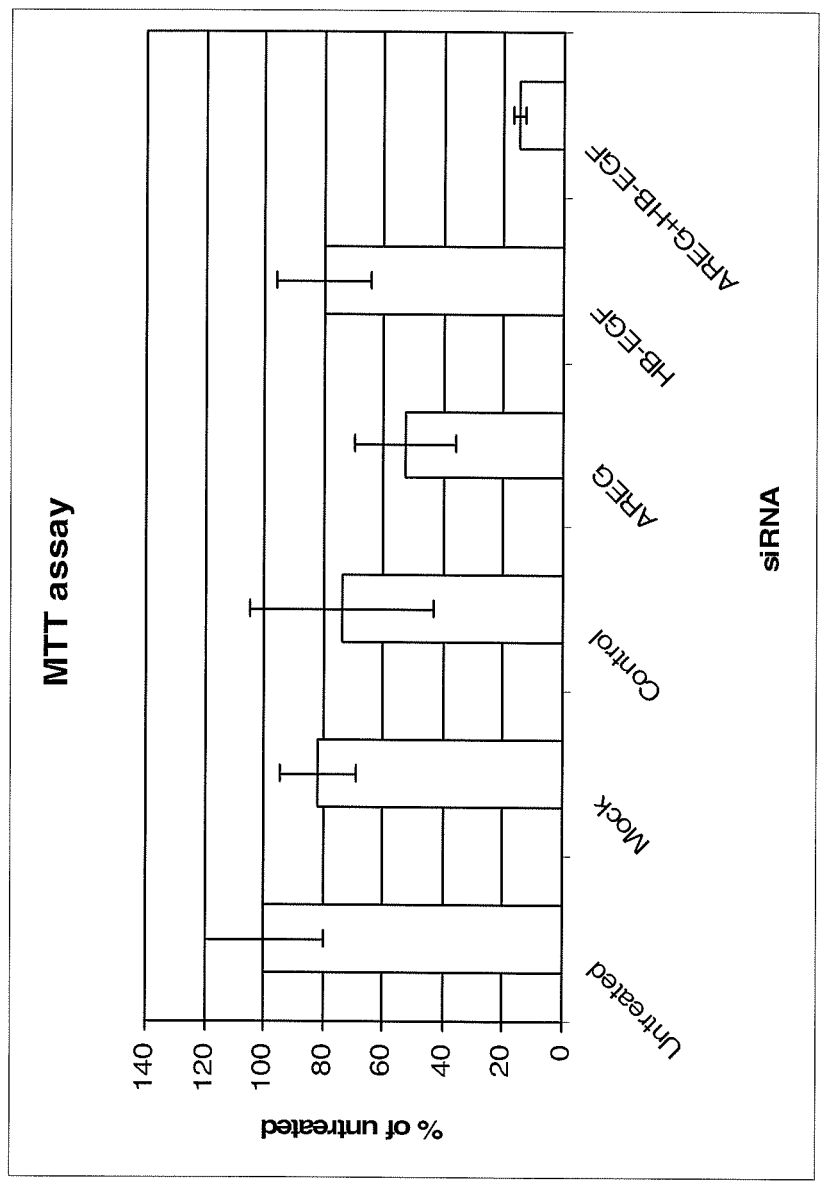

The effect of knocking down the expression of AREG and HBEGF by RNA interference on cell growth was investigated by performing a cell viability assay (FIG. 1). The effect of AREG siRNA was 50% reduction in cell growth and with HBEGF siRNA alone an effect of 20% reduction was observed. When both siRNA are added to the cells in combination an 85% reduction in cell growth was seen. This suggests that targeting these two EGF-like ligands in cancer can attenuate cell growth.

Figure 2:
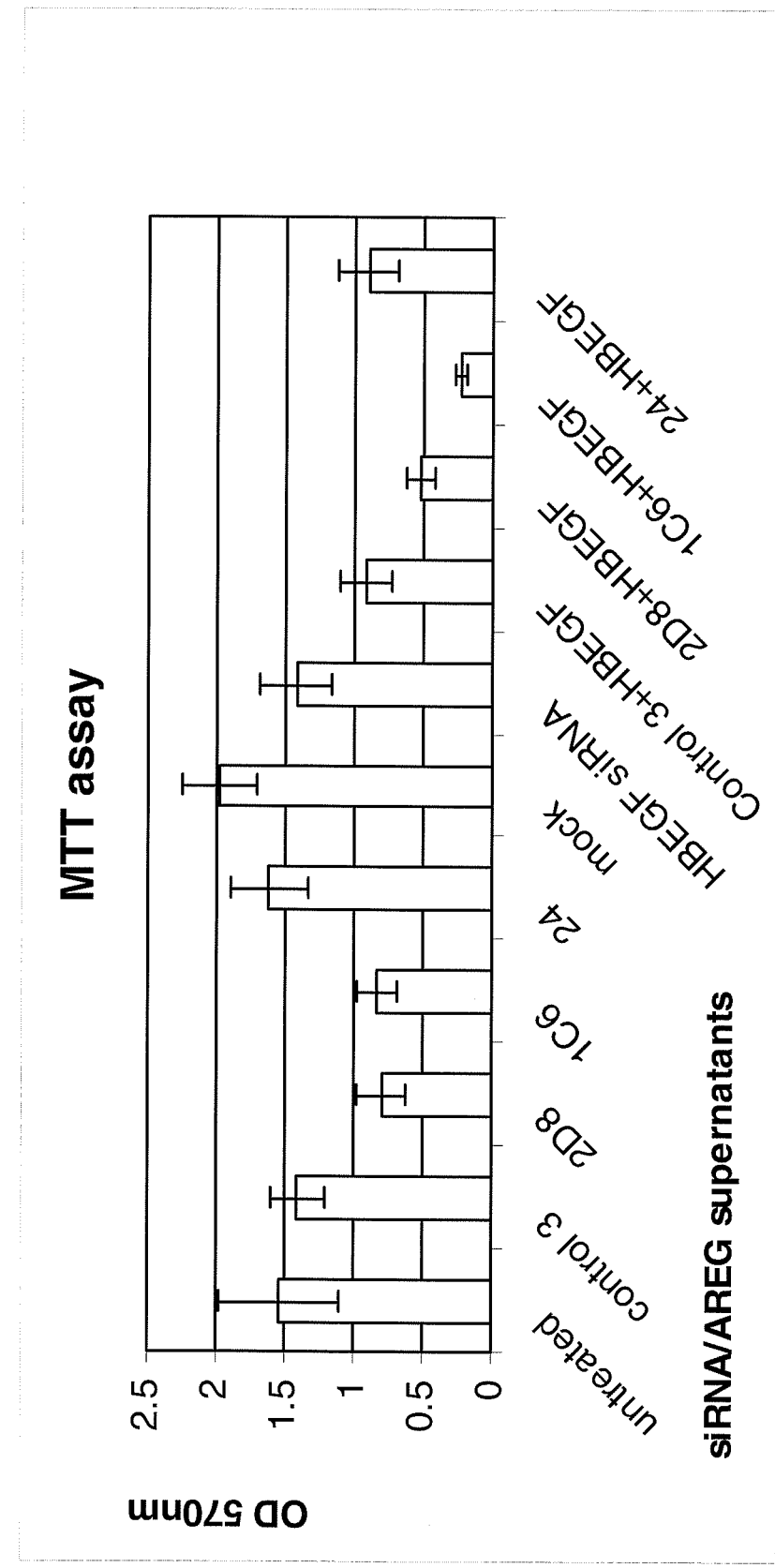

An AREG monoclonal antibody was produced and used in combination with HBEGF siRNA to see if the same effect could be observed on cell growth. The cell viability results showed that both 6E11 1E9 2D8/6E11 1E9 106 alone and HBEGF alone had a 50% reduction on growth. When added in combination a reduction between 10% and 30% in cell viability was seen (FIG. 2). The RI values were calculated to see if the effect observed was synergistic. The RI value is calculated as the ratio of expected survival ($S_{exp}$ defined as the product of the survival observed with drug A alone and the survival observed with drug B alone) to the observed cell survival ($S_{obs}$) for the combination of A and B. (RI=$S_{exp}$/$S_{obs}$). Synergism is defined as RI>1. The RI value for AREG antibody in combination with HBEGF siRNA was calculated as being 2 for 6E11 1E9 2D8 and 5 for 6E11 1E9 106. Collectively these results show that by targeting both HBEGF and AREG in the treatment of colorectal cancer cells a synergistic effect on the attenuation of cell growth is produced.

Development and Characterization of AREG/HBEGF Bispecific Antibodies

Figure 3:
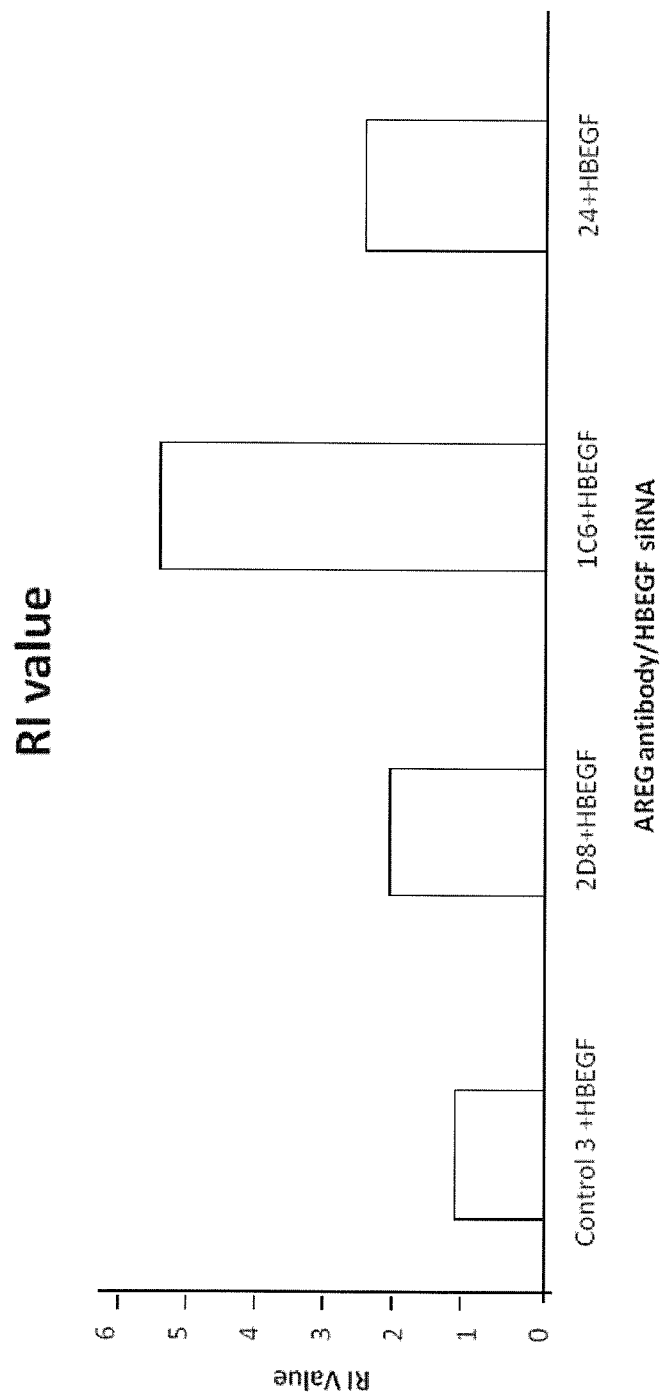
Figure 4:
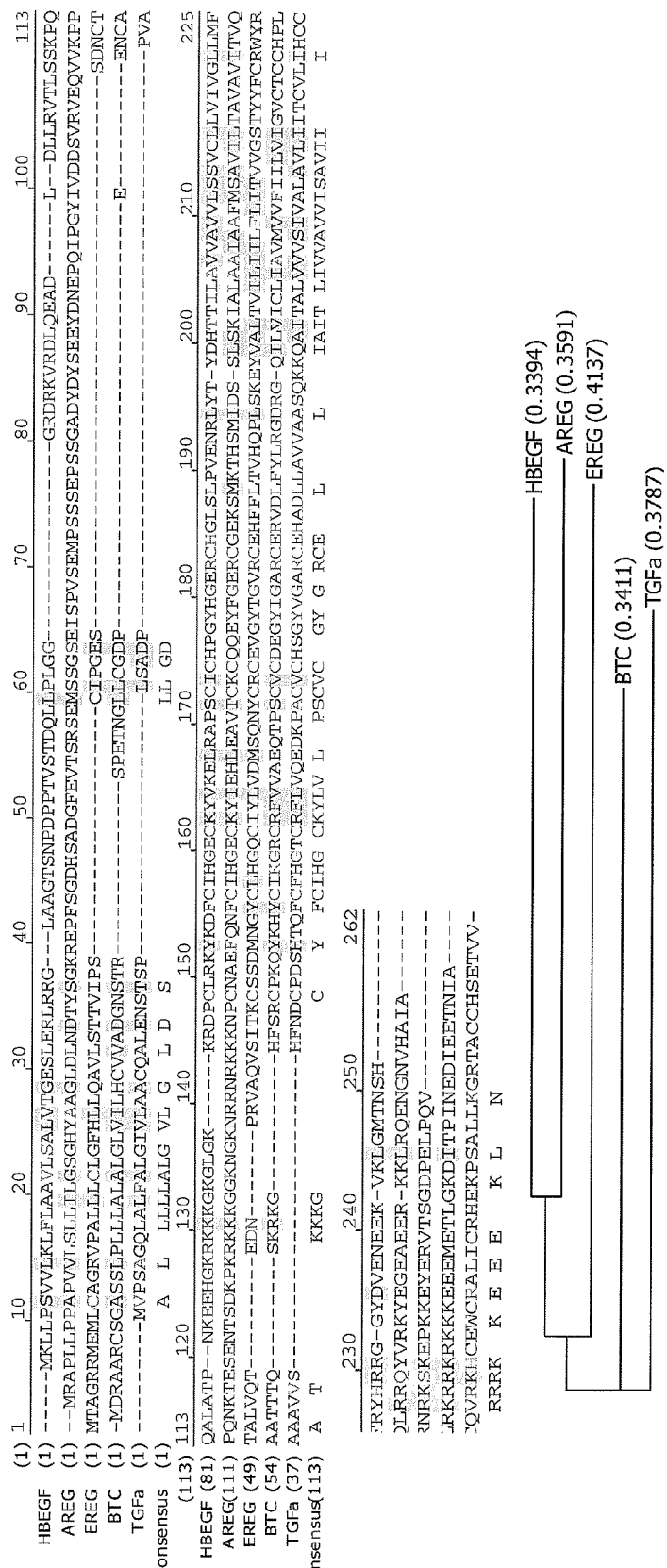

The alignment of five of the EGF-like ligands shows that there is little homology between the ligands except for 6 conserved cysteine residues which are found in the EGF domain and are believed to be involved in ligand binding (FIG. 3). FIG. 4 shows the alignment of AREG and HBEGF and also shows a region that was selected for antibody production. It was thought that one antibody could be produced that targets both AREG and HBEGF. The recombinant protein to this region was produced in E. coli and used to immunize mice.

A panel of murine monoclonal antibodies was raised to the recombinant protein and characterized by ELISA, FACS and western blot. The monoclonal antibodies were screened by an ELISA against recombinant HBEGF and recombinant AREG proteins made in house and also commercially available proteins (R & D systems) and also a negative control made in similar manner.

Figure 9:
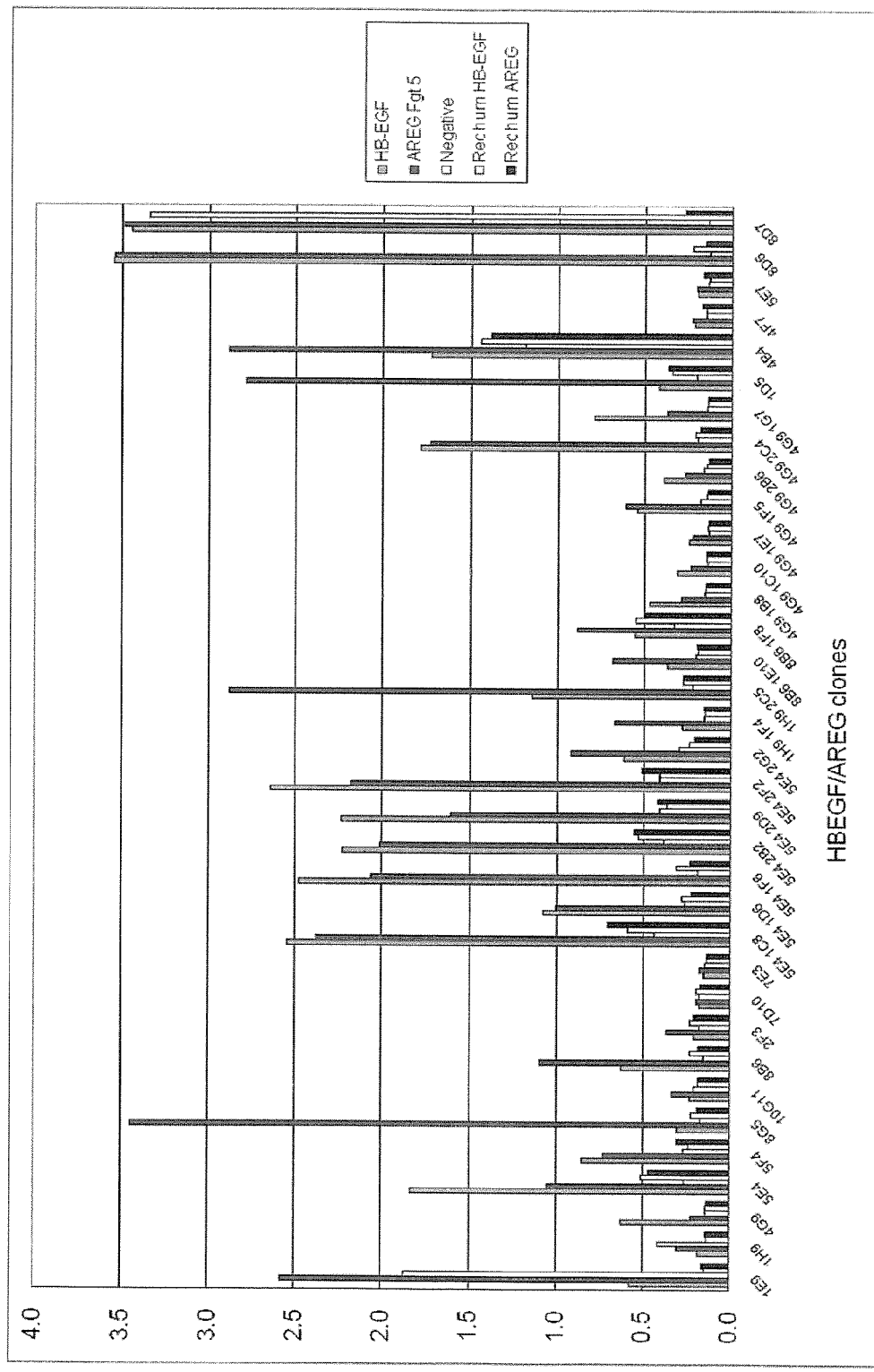
Figure 10:
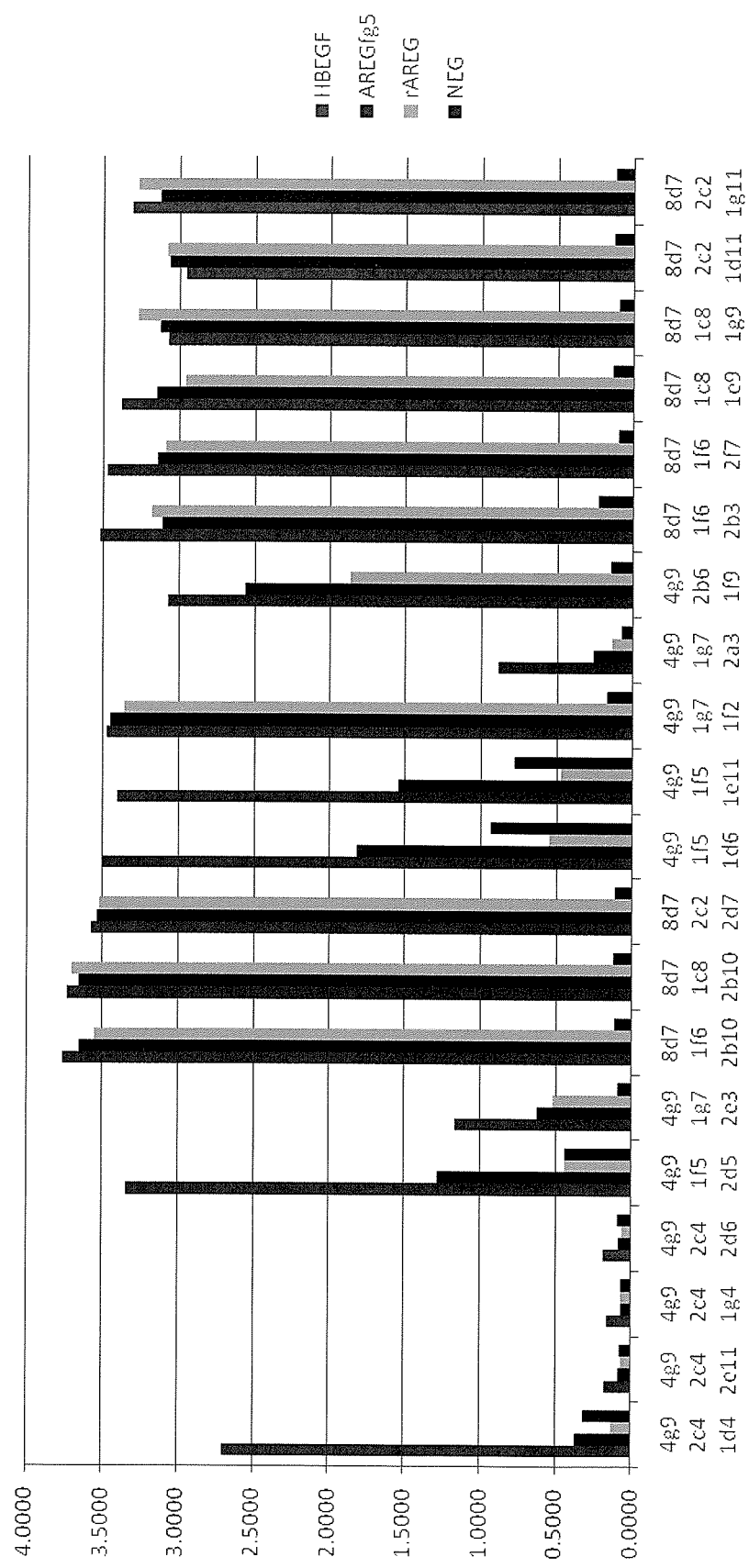
FIG. 10 illustrates ELISA screening of HBEGF/AREG monoclonal antibodies against recombinant protein made in house for AREG and HBEGF and R and D systems recombinant protein for human AREG and HBEGF. Monoclonal antibodies were also screened against a negative control protein produced by similar method; (from left to right for each antibody-HBEGF, AREGfg5, rAREG, NEG)
Figure 11:
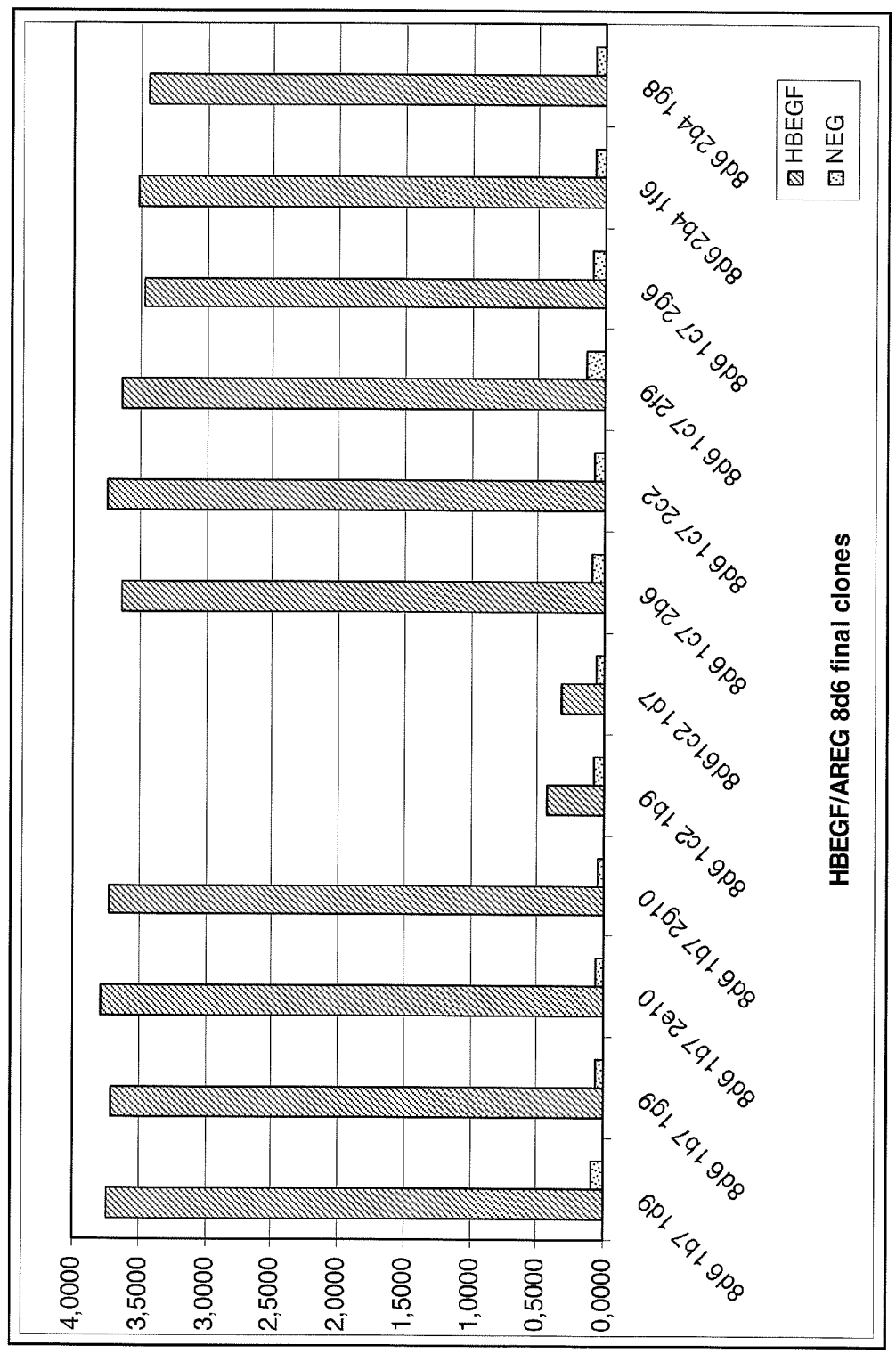
FIG. 11 illustrates ELISA screening of HBEGF/AREG monoclonal antibodies against recombinant protein made in house for HBEGF and R and D systems recombinant protein for human HBEGF. Monoclonal antibodies were also screened against a negative control protein produced by similar method.

ELISA results are shown in FIGS. 9-11 and show that the antibodies are specific for both AREG and HBEGF when compared to negative control. These antibodies have been tested by western blot and are able to detect endogenous proteins as shown in FIG. 12.

FIG. 13 shows immunofluorescent staining results using a bi-specific antibody

FACS analysis using the bi-specific antibodies show that they bind to the surface of the cells and that the binding increases with chemotherapy treatment (FIGS. 14a, and 14b).
Inhibition of Ligand-Stimulated Phosphorylation of EGFR by Cross Specific Antibody.

The effect of the cross-specific antibodies against AREG and HBEGF on the EGFR pathway was assessed by investigating the phosphorylation of the EGFR. The antibody was pre-incubated with the HBEGF ligand before addition to cells. It can be clearly observed that the cross-specific antibody inhibits the HBEGF stimulated phosphorylation of EGFR on Tyrosine 1068.

FIG. 15 shows the inhibition of ligand stimulated phosphorylation in both the MDA-MB231 breast cancer cell line and the colorectal cancer cell line HCT116. The reduction in phosphorylation in HCT116 at antibody concentration of 1000 nM (FIG. 15b lane 5) seems to be below the basal level (FIG. 15b, lane 1). FIG. 16 shows similar results in a different colorectal cancer cell line, LoVo.
Inhibition of Ligand Stimulated Growth by Cross Specific Antibody.

Recombinant HBEGF ligand stimulated the growth of a colorectal cancer cell line LoVo by approximately 60%. An isotype control and cross-specific antibody were pre-incubated with the recombinant HBEGF for 1 hr before addition to the cells. The isotype control antibody had no effect on the stimulation of growth by HBEGF. The cross-specific antibody (1E9) was able to inhibit the ligand induced growth in a dose dependent manner (FIG. 17). 300 nM of cross-specific antibody prevents any stimulation of cell growth by HBEGF. This result shows that the antibody binds to the ligand and prevents the function of the ligand.
Attenuation of Cell Growth by Cross-Specific Antibody.

When cross-specific antibody is added to the cells alone at a concentration of 100 nM a 40% reduction in cell growth was observed (FIG. 18a). The growth was attenuated further when antibody was added in combination with 10 µM cpt-11 (FIG. 18b). The cell growth reduced to 40% of the growth of isotype control in combination with chemotherapy. This shows that dual targeting of both AREG and HBEGF has a significant effect on cell growth alone and in combination with conventional chemotherapies in cancer including colorectal cancer.

Figures 20A, 20B:
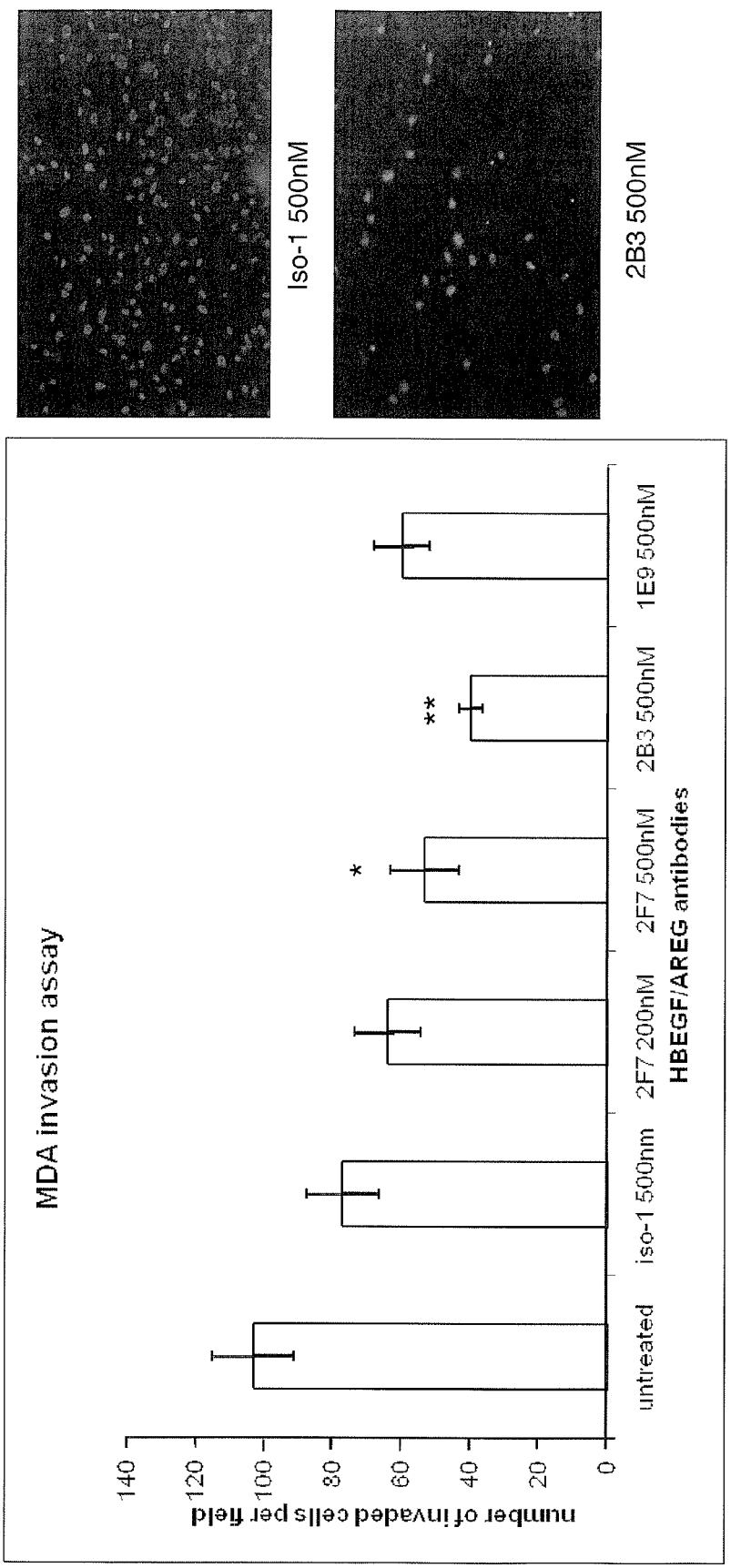

The cross-specific antibody was compared to Cetuximab (C225) a humanised antibody that inhibits EGFR and has been approved for use in colorectal cancer. When the cross-specific antibody was used at the same concentration as that recommended for C225 in cell growth assays, a 25% reduction is cell growth was observed with the cross-specific while no significant effect was observed with C225 (FIG. 19). The antibodies were used in combination with cpt-11 at a dose of 5 µM (IC30) and only with the cross-specific antibody showed a significant reduction in cell growth. A 43% reduction in cell growth was observed when using the cross-specific antibody in combination with chemotherapy in comparison to C225 and isotype control antibody. The C225 showed no effect compared to the isotype control antibody. These results suggest that targeting the ligands may be more beneficial than targeting the receptor as one may also inhibit non EGFR related ligand activities.
Reduction in Cancer Cell Invasion and Migration by Cross-Specific Antibody Cell invasion and migration were investigated in the MDA-MB231 breast cancer cell line by Boyden Chamber invasion assay and wound scratch migration assay. FIG. 20a shows the results of the Boyden chamber invasion assay. The cross-specific antibodies resulted in a significant reduction in the number of cells invading compared to isotype control. The antibodies reduced the cell invasion by between 30% and 50%. FIG. 20b shows images that were taken of the invading cells and a clear difference between isotype and cross-specific antibodies can be seen.

The wound scratch assay showed that the cross-specific antibody kept the wound open more than the isotype control. The width of the wound with cross-specific antibody was 300% wider than that of the isotype control. The wound in the untreated cells had completely closed over. These results suggest that dual targeting of AREG and HBEGF have effects on different hallmarks of cancer and not just cell growth.
Dual Targeting of AREG and HBEGF Inhibits Angiogenesis The HUVEC cell line was used to investigate if targeting both AREG and HBEGF would have any effect on angiogenesis. An invasion assay using Boyden chamber and the HUVEC cells was used. The cross-specific antibodies reduced the number of cells invading by 30% compared to the isotype control antibody (FIG. 22).

Another angiogenesis assay used was the tube assay. The HUVEC cells were seeded in wells and they form tube like structures which can be seen in FIG. 23 untreated image. An anti-angiogenic response was observed with the cross-specific antibody which can be seen as a disruption to the tube structures in the image (FIG. 23). The branch points around nodes were counted and represented on a graph (FIG. 23). An anti-angiogenic effect is observed when there is a decrease in number of 3 and 4 branch points and increase in the number of 1 and 2 branch points. This can clearly be seen with the cross-specific antibody compared to isotype control antibody and untreated.

The cross-specific antibodies showed significant results in a HUVEC migration assay. There was a 20% reduction in the number of cells migrating in the Boyden chamber compared to the isotype control antibody. These results all suggest that the cross-specific antibodies may significantly reduce angiogenesis.

The inventors have made a panel of monoclonal antibodies that bind to both AREG and HBEGF. These antibodies show inhibitory effects on cell growth, cell invasion and cell migration and are expected to show inhibitory effects.

All documents referred to in this specification are herein incorporated by reference. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. An isolated antibody molecule which binds HBEGF and AREG and inhibits the activity of HBEGF and the activity of AREG, wherein the antibody molecule comprises the three CDRs of the VH sequence shown as SEQ ID NO:7 and the three CDRs of the VL sequence shown as SEQ ID NO:8.

2. The isolated antibody molecule according to claim 1, wherein the antibody molecule comprises the VH domain shown as SEQ ID NO:7 and/or the VL sequence shown as SEQ ID NO:8.

3. The isolated antibody molecule according to claim 1, wherein said antibody molecule does not bind one or more of epiregulin (EREG), betacellulin (BTC) or TGFα.

4. The isolated antibody molecule according to claim 1, wherein said antibody molecule does not bind any of epiregulin (EREG), betacellulin (BTC) or TGFα.

5. The isolated antibody molecule according to claim 1, wherein the antibody molecule binds the amino acid sequence shown as SEQ ID NO:1 and the amino acid sequence shown as SEQ ID NO:2.

6. The isolated antibody molecule according to claim 1 wherein the antibody molecule is a monoclonal antibody.

7. A pharmaceutical composition comprising the isolated antibody molecule according to claim 1.

8. The pharmaceutical composition according to claim 7, wherein the composition further comprises a chemotherapeutic agent and/or an angiogenesis inhibitor.

9. A kit comprising:
(i) the isolated antibody molecule according to claim 1; and
(ii) a chemotherapeutic agent and/or an angiogenesis inhibitor for simultaneous, sequential or separate administration.

10. The pharmaceutical composition according to claim 8, wherein said chemotherapeutic agent is selected from the group consisting of antimetabolites, topoisomerase inhibitors, alkylating agents, anthracyclines, and plant alkaloids.

11. The pharmaceutical composition according to claim 8, wherein the angiogenesis inhibitor is selected from the group consisting of sorafenib, sunitinib, PTK787, AG013676, ZD6474 and VEGF-Trap, AG-13958, VEGF siRNA, squalamine, anecortave, and combretastatin.

* * * * *

SEQUENCE LISTING

<160> NUMBER OF SEQ ID NOS: 17

<210> SEQ ID NO 1
<211> LENGTH: 44
<212> TYPE: PRT
<213> ORGANISM: Homo sapiens

<400> SEQUENCE: 1

Lys Lys Asn Pro Cys Asn Ala Glu Phe Gln Asn Phe Cys Ile His Gly
1               5                   10                  15

Glu Cys Lys Tyr Ile Glu His Leu Glu Ala Val Thr Cys Lys Cys Gln
            20                  25                  30

Gln Glu Tyr Phe Gly Glu Arg Cys Gly Glu Lys Ser
        35                  40

<210> SEQ ID NO 2
<211> LENGTH: 41
<212> TYPE: PRT
<213> ORGANISM: Homo sapiens

<400> SEQUENCE: 2

Lys Arg Asp Pro Cys Leu Arg Lys Tyr Lys Asp Phe Cys Ile His Gly
1               5                   10                  15

Glu Cys Lys Tyr Val Lys Glu Leu Arg Ala Pro Ser Cys Ile Cys His
            20                  25                  30

Pro Gly Tyr His Gly Glu Arg Cys His
        35                  40

<210> SEQ ID NO 3
<211> LENGTH: 168
<212> TYPE: PRT
<213> ORGANISM: Mus musculus

<400> SEQUENCE: 3

Met Glu Cys Asn Trp Ile Leu Pro Phe Ile Leu Ser Val Thr Ser Gly
1               5                   10                  15

Val Tyr Ser Gln Val Gln Leu Gln Gln Ser Gly Ala Glu Leu Ala Arg
            20                  25                  30

Pro Gly Ala Ser Val Lys Leu Ser Cys Lys Ala Ser Gly Tyr Thr Phe
        35                  40                  45

Thr Arg Tyr Trp Met Gln Trp Ile Lys Gln Arg Pro Gly Gln Gly Leu
    50                  55                  60

Glu Trp Ile Gly Ala Ile Tyr Pro Gly Asn Gly Asp Ile Arg Tyr Thr
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Ala Ser Glu Asp Ser Ala Val
            100                 105                 110

Tyr Tyr Cys Ala Arg Gly Thr Thr Pro Ser Ser Tyr Trp Gly Gln Gly
        115                 120                 125

Thr Leu Val Thr Val Ser Ala Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe
                165

<210> SEQ ID NO 4

<211> LENGTH: 167
<212> TYPE: PRT
<213> ORGANISM: Mus musculus

<400> SEQUENCE: 4

```
Met Met Ser Pro Ala Gln Phe Leu Phe Leu Leu Val Leu Trp Ile Arg
1               5                   10                  15

Glu Thr Ser Gly Asp Val Val Met Thr Gln Thr Pro Leu Thr Leu Ser
                20                  25                  30

Val Ser Ile Gly Gln Pro Ala Ser Ile Ser Cys Lys Ser Ser Gln Ser
            35                  40                  45

Leu Leu Asp Ser Asp Gly Lys Thr Tyr Leu Asn Trp Leu Leu Gln Arg
50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Trp Thr Phe Gly Gly Gly Thr Lys
        115                 120                 125

Leu Glu Ile Lys Arg Ala Asp Ala Ala Pro Thr Val Ser Ile Phe Pro
130                 135                 140

Pro Ser Ser Glu Gln Leu Thr Ser Gly Gly Ala Ser Val Val Cys Phe
145                 150                 155                 160

Leu Asn Asn Phe Tyr Pro Lys
                165
```

<210> SEQ ID NO 5
<211> LENGTH: 154
<212> TYPE: PRT
<213> ORGANISM: Mus musculus
<220> FEATURE:
<221> NAME/KEY: misc_feature
<222> LOCATION: (154)..(154)
<223> OTHER INFORMATION: Xaa can be any naturally occurring amino acid

<400> SEQUENCE: 5

```
Met Glu Trp Ser Trp Val Ile Leu Phe Leu Met Ala Val Val Thr Gly
1               5                   10                  15

Val Asn Ser Glu Val Gln Leu Gln Gln Ser Gly Ala Glu Leu Val Arg
                20                  25                  30

Pro Gly Ala Leu Val Lys Leu Ser Cys Lys Ala Ser Gly Phe Asn Ile
            35                  40                  45

Lys Asp Ser Tyr Ile His Trp Val Asn Gln Arg Pro Glu Gln Gly Leu
50                  55                  60

Glu Trp Ile Gly Trp Ile Asp Pro Glu Asn Gly Asn Thr Ile Tyr Asp
65                  70                  75                  80

Pro Lys Phe Gln Gly Lys Ala Ser Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Val Ser Ala Ser Tyr Arg Tyr Gly Phe Ser Tyr Trp Gly
        115                 120                 125

Gln Gly Thr Leu Val Thr Val Ser Ala Ala Lys Thr Thr Pro Pro Ser
130                 135                 140

Val Tyr Pro Trp Val Pro Gly Ser Leu Xaa
```

```
<210> SEQ ID NO 6
<211> LENGTH: 101
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (100)..(101)
<223> OTHER INFORMATION: Xaa can be any naturally occurring amino acid

<400> SEQUENCE: 6

Xaa Ala Asp Xaa Ile Ser Ile Ser Cys Arg Ser Asn Lys Ser Leu Leu
1               5                   10                  15

His Thr Asn Gly Asn Thr Tyr Leu Tyr Trp Phe Leu Gln Arg Pro Gly
            20                  25                  30

Gln Ser Pro Gln Leu Leu Ile Tyr Arg Met Ser Asn Leu Ala Ser Gly
        35                  40                  45

Val Pro Asp Arg Phe Ser Gly Ser Gly Ser Gly Thr Ala Phe Thr Leu
50                  55                  60

Arg Ile Ser Arg Val Glu Ala Glu Asp Val Gly Val Tyr Tyr Cys Met
65                  70                  75                  80

Gln His Leu Glu Tyr Pro Tyr Thr Phe Gly Gly Gly Thr Lys Leu Glu
                85                  90                  95

Ile Lys Arg Xaa Xaa
            100

<210> SEQ ID NO 7
<211> LENGTH: 153
<212> TYPE: PRT
<213> ORGANISM: Mus musculus

<400> SEQUENCE: 7

Met Lys Cys Ser Trp Ile Ile Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Asp Ser Tyr Ile His Trp Val Asn Gln Arg Pro Glu Gln Gly Leu
50                  55                  60

Glu Trp Ile Gly Trp Ile Asp Pro Glu Asn Gly Asn Thr Ile Tyr Asp
65                  70                  75                  80

Pro Lys Phe Gln Gly Lys Ala Ser Ile Thr Ala Asp Thr Ser Ser Asn
                85                  90                  95

Thr Ala Tyr Leu Gln Leu Ser Ser Leu Thr Ser Glu Asp Thr Ala Val
                100                 105                 110

Tyr Tyr Cys Val Ser Ala Ser Tyr Arg Tyr Gly Phe Ser Tyr Trp Gly
                115                 120                 125

Gln Gly Thr Leu Val Thr Val Ser Ala Ala Lys Thr Thr Pro Pro Pro
            130                 135                 140

Val Tyr Pro Leu Ala Pro Gly Ser Leu
```

```
145                  150

<210> SEQ ID NO 8
<211> LENGTH: 150
<212> TYPE: PRT
<213> ORGANISM: Mus musculus

<400> SEQUENCE: 8

Met Arg Ala Pro Ala Gln Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Asn Lys Ser
        35                  40                  45

Leu Leu His Thr Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Lys Leu Gly
145                 150

<210> SEQ ID NO 9
<211> LENGTH: 153
<212> TYPE: PRT
<213> ORGANISM: Mus musculus

<400> SEQUENCE: 9

Met Lys Cys Ser Trp Val Met Phe Phe Leu Met Ala Val Val Thr Gly
1               5                   10                  15

Val Asn Ser Glu Val Gln Leu Gln Gln Ser Gly Ala Glu Leu Val Arg
            20                  25                  30

Pro Gly Ala Leu Val Lys Leu Ser Cys Lys Ala Ser Gly Phe Asn Ile
        35                  40                  45

Lys Asp Ser Tyr Ile His Trp Val Asn Gln Arg Pro Glu Gln Gly Leu
    50                  55                  60

Glu Trp Ile Gly Trp Ile Asp Pro Glu Asn Gly Asn Thr Ile Tyr Asp
65                  70                  75                  80

Pro Lys Phe Gln Gly Lys Ala Ser Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Val Ser Ala Ser Tyr Arg Tyr Gly Phe Ser Tyr Trp Gly
        115                 120                 125

Gln Gly Thr Leu Val Thr Val Ser Ala Ala Lys Thr Thr Pro Pro Pro
    130                 135                 140

Val Tyr Pro Leu Ala Pro Gly Ser Leu
145                 150
```

-continued

```
<210> SEQ ID NO 10
<211> LENGTH: 150
<212> TYPE: PRT
<213> ORGANISM: Mus musculus

<400> SEQUENCE: 10

Met Arg Pro Pro Leu Ser Phe Leu Gly Leu Leu Val Leu Trp Ile Pro
1               5                   10                  15

Gly Ala Ile Gly Asp Ile Val Met Thr Gln Ala Ala Pro Ser Val Pro
            20                  25                  30

Val Thr Pro Gly Glu Ser Val Ser Ile Ser Cys Arg Ser Asn Lys Ser
        35                  40                  45

Leu Leu His Thr Asn Gly Asn Thr Tyr Leu Tyr Trp Phe Leu Gln Arg
    50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Tyr Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Lys Leu Gly
145                 150

<210> SEQ ID NO 11
<211> LENGTH: 208
<212> TYPE: PRT
<213> ORGANISM: Homo sapiens

<400> SEQUENCE: 11

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
```

```
                180                 185                 190
Asp Val Glu Asn Glu Lys Val Lys Leu Gly Met Thr Asn Ser His
        195                 200                 205

<210> SEQ ID NO 12
<211> LENGTH: 252
<212> TYPE: PRT
<213> ORGANISM: Homo sapiens

<400> SEQUENCE: 12

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
            20                  25                  30

Tyr Ser Gly Lys Arg Glu Pro Phe Ser Gly Asp His Ser Ala Asp Gly
        35                  40                  45

Phe Glu Val Thr Ser Arg Ser Glu Met Ser Ser Gly Ser Glu Ile Ser
    50                  55                  60

Pro Val Ser Glu Met Pro Ser Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
        115                 120                 125

Lys Gly Gly Lys Asn Gly Lys Asn Arg Arg Asn Arg Lys Lys Lys Asn
    130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met
        195                 200                 205

Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Glu Arg Lys Lys
225                 230                 235                 240

Leu Arg Gln Glu Asn Gly Asn Val His Ala Ile Ala
                245                 250

<210> SEQ ID NO 13
<211> LENGTH: 169
<212> TYPE: PRT
<213> ORGANISM: Homo sapiens

<400> SEQUENCE: 13

Met Thr Ala Gly Arg Arg Met Glu Met Leu Cys Ala Gly Arg Val Pro
1               5                   10                  15

Ala Leu Leu Leu Cys Leu Gly Phe His Leu Leu Gln Ala Val Leu Ser
            20                  25                  30

Thr Thr Val Ile Pro Ser Cys Ile Pro Gly Glu Ser Ser Asp Asn Cys
        35                  40                  45

Thr Ala Leu Val Gln Thr Glu Asp Asn Pro Arg Val Ala Gln Val Ser
```

```
            50                  55                  60
Ile Thr Lys Cys Ser Ser Asp Met Asn Gly Tyr Cys Leu His Gly Gln
 65                  70                  75                  80

Cys Ile Tyr Leu Val Asp Met Ser Gln Asn Tyr Cys Arg Cys Glu Val
                 85                  90                  95

Gly Tyr Thr Gly Val Arg Cys Glu His Phe Phe Leu Thr Val His Gln
                100                 105                 110

Pro Leu Ser Lys Glu Tyr Val Ala Leu Thr Val Ile Leu Ile Ile Leu
                115                 120                 125

Phe Leu Ile Thr Val Val Gly Ser Thr Tyr Tyr Phe Cys Arg Trp Tyr
130                 135                 140

Arg Asn Arg Lys Ser Lys Glu Pro Lys Lys Glu Tyr Glu Arg Val Thr
145                 150                 155                 160

Ser Gly Asp Pro Glu Leu Pro Gln Val
                165
```

<210> SEQ ID NO 14
<211> LENGTH: 178
<212> TYPE: PRT
<213> ORGANISM: Homo sapiens

<400> SEQUENCE: 14

```
Met Asp Arg Ala Ala Arg Cys Ser Gly Ala Ser Ser Leu Pro Leu Leu
  1               5                  10                  15

Leu Ala Leu Ala Leu Gly Leu Val Ile Leu His Cys Val Val Ala Asp
                 20                  25                  30

Gly Asn Ser Thr Arg Ser Pro Glu Thr Asn Gly Leu Leu Cys Gly Asp
                 35                  40                  45

Pro Glu Glu Asn Cys Ala Ala Thr Thr Thr Gln Ser Lys Arg Lys Gly
                 50                  55                  60

His Phe Ser Arg Cys Pro Lys Gln Tyr Lys His Tyr Cys Ile Lys Gly
 65                  70                  75                  80

Arg Cys Arg Phe Val Val Ala Glu Gln Thr Pro Ser Cys Val Cys Asp
                 85                  90                  95

Glu Gly Tyr Ile Gly Ala Arg Cys Glu Arg Val Asp Leu Phe Tyr Leu
                100                 105                 110

Arg Gly Asp Arg Gly Gln Ile Leu Val Ile Cys Leu Ile Ala Val Met
                115                 120                 125

Val Val Phe Ile Ile Leu Val Ile Gly Val Cys Thr Cys Cys His Pro
130                 135                 140

Leu Arg Lys Arg Arg Lys Arg Lys Lys Lys Glu Glu Met Glu Thr
145                 150                 155                 160

Leu Gly Lys Asp Ile Thr Pro Ile Asn Glu Asp Ile Glu Glu Thr Asn
                165                 170                 175

Ile Ala
```

<210> SEQ ID NO 15
<211> LENGTH: 160
<212> TYPE: PRT
<213> ORGANISM: Homo sapiens

<400> SEQUENCE: 15

```
Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
            20                  25                  30

Asp Pro Pro Val Ala Ala Val Val Ser His Phe Asn Asp Cys Pro
                35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
                100                 105                 110

Val Leu Ile Ile Thr Cys Val Leu Ile His Cys Cys Gln Val Arg Lys
            115                 120                 125

His Cys Glu Trp Cys Arg Ala Leu Ile Cys Arg His Glu Lys Pro Ser
        130                 135                 140

Ala Leu Leu Lys Gly Arg Thr Ala Cys Cys His Ser Glu Thr Val Val
145                 150                 155                 160

<210> SEQ ID NO 16
<211> LENGTH: 83
<212> TYPE: PRT
<213> ORGANISM: Artificial Sequence
<220> FEATURE:
<223> OTHER INFORMATION: consensus sequence derived from amino acid
      sequence alignment of HBEGF, AREG, EREG, BTC, TGFA

<400> SEQUENCE: 16

Ala Leu Leu Leu Leu Ala Leu Gly Val Leu Gly Leu Asp Ser Leu
1               5                   10                  15

Leu Gly Asp Pro Val Ala Ala Thr Lys Lys Lys Gly Cys Tyr Phe Cys
            20                  25                  30

Thr His Gly Cys Lys Tyr Leu Val Leu Pro Ser Cys Val Cys Gly Tyr
        35                  40                  45

Gly Arg Cys Glu Leu Leu Ile Ala Thr Thr Leu Ile Val Val Ala Val
    50                  55                  60

Val Ile Ser Ala Val Ile Ile Arg Arg Lys Lys Glu Glu
65                  70                  75                  80

Lys Leu Asn

<210> SEQ ID NO 17
<211> LENGTH: 89
<212> TYPE: PRT
<213> ORGANISM: Artificial Sequence
<220> FEATURE:
<223> OTHER INFORMATION: consensus sequence derived from amino acid
      sequence alignment of AREG and HBEGF

<400> SEQUENCE: 17

Leu Pro Ala Val Leu Leu Gly Leu Gly Ala Gly Asp Val Ser Ser Leu
1               5                   10                  15

Gly Gly Asp Asp Asp Asp Leu Arg Val Lys Pro Thr Asn Asp Lys
            20                  25                  30

Arg Lys Lys Lys Gly Gly Lys Lys Pro Cys Phe Phe Cys Ile His
        35                  40                  45

Gly Glu Cys Lys Tyr Ile Leu Ala Ser Cys Cys Tyr Gly Glu Arg Cys
```

-continued

```
            50                  55                  60
Ser Leu Ile Ser Leu Ala Ile Ala Leu Ser Ala Val Leu Ile Ile Met
65                  70                  75                  80

Tyr Asp Glu Glu Glu Lys Lys Leu Asn
                85
```